(12) United States Patent
Zhao et al.

(10) Patent No.: US 10,561,337 B2
(45) Date of Patent: Feb. 18, 2020

(54) RAPID 3D DYNAMIC ARTERIAL SPIN LABELING WITH A SPARSE MODEL-BASED IMAGE RECONSTRUCTION

(71) Applicant: University of Virginia Patent Foundation, Charlottesville, VA (US)

(72) Inventors: Li Zhao, Boston, MA (US); Craig Meyer, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 852 days.

(21) Appl. No.: 15/227,825

(22) Filed: Aug. 3, 2016

(65) Prior Publication Data

US 2017/0035319 A1 Feb. 9, 2017

Related U.S. Application Data

(60) Provisional application No. 62/200,943, filed on Aug. 4, 2015, provisional application No. 62/323,394, filed on Apr. 15, 2016.

(51) Int. Cl.
*A61B 5/055* (2006.01)
*A61B 5/026* (2006.01)
(Continued)

(52) U.S. Cl.
CPC ............ *A61B 5/055* (2013.01); *A61B 5/0042* (2013.01); *A61B 5/0263* (2013.01);
(Continued)

(58) Field of Classification Search
USPC .......................................... 600/419
See application file for complete search history.

(56) References Cited

U.S. PATENT DOCUMENTS 7,583,082 B1   9/2009  Hu et al.
7,642,777 B1   1/2010  Meyer et al.
(Continued)

FOREIGN PATENT DOCUMENTS

WO    2010062557 A1    6/2010
WO    2012145547 A1    10/2012
(Continued)

OTHER PUBLICATIONS

Aharon, M., et al., 2006. "K-SVD: An Algorithm for Designing Overcomplete Dictionaries for Sparse Representation." IEEE Trans. Signal Process. vol. 54, No. 11, pp. 4311-4322.
(Continued)

*Primary Examiner* — Pierre E Elisca
(74) *Attorney, Agent, or Firm* — Meunier Carlin & Curfman LLC

(57) ABSTRACT

Methods, systems, and computer-readable media for rapid 3D dynamic arterial spin labeling with a sparse model-based image reconstruction are disclosed. In one embodiment, a method includes acquiring magnetic resonance data associated with an area of interest of a subject. The magnetic resonance data includes associated with arterial spin labeling (ASL) of the area of interest. The method also includes performing image reconstruction on the acquired resonance data. The image reconstruction includes compressed sensing enforcing a model-based sparsity constraint, where the model-based sparsity constraint is based on an ASL signal prototype dictionary.

20 Claims, 15 Drawing Sheets
(13 of 15 Drawing Sheet(s) Filed in Color)

(51) Int. Cl.
   A61B 5/00      (2006.01)
   G01R 33/563    (2006.01)
   G01R 33/561    (2006.01)
   G01R 33/48     (2006.01)
(52) U.S. Cl.
   CPC .... *G01R 33/5611* (2013.01); *G01R 33/56366* (2013.01); *G01R 33/4826* (2013.01); *G06K 2209/05* (2013.01)

(56) References Cited

U.S. PATENT DOCUMENTS

| | | |
|---|---|---|
| 7,888,935 B1 | 2/2011 | Tan et al. |
| 8,026,720 B1 | 9/2011 | Chen et al. |
| 8,094,907 B1 | 1/2012 | Meyer et al. |
| 8,238,634 B1 | 8/2012 | Meyer et al. |
| 8,306,289 B1 | 11/2012 | Meyer et al. |
| 8,440,167 B2 | 5/2013 | Beller et al. |
| 9,183,626 B2 | 11/2015 | Zhao et al. |
| 2013/0278261 A1 | 10/2013 | Fielden et al. |
| 2013/0307536 A1 | 11/2013 | Feng et al. |
| 2014/0044335 A1 | 2/2014 | Johnson et al. |
| 2014/0152304 A1 | 6/2014 | Fielden et al. |
| 2014/0219531 A1* | 8/2014 | Epstein ............ G01R 33/56308 382/131 |
| 2014/0364723 A1 | 12/2014 | Meyer et al. |
| 2015/0282719 A1 | 10/2015 | Fielden et al. |
| 2015/0282733 A1 | 10/2015 | Fielden et al. |
| 2015/0285889 A1 | 10/2015 | Chen et al. |
| 2015/0287222 A1 | 10/2015 | Zhao et al. |
| 2015/0316630 A1 | 11/2015 | Zhao et al. |
| 2016/0098835 A1 | 4/2016 | Zhao et al. |
| 2016/0148378 A1 | 5/2016 | Salerno et al. |
| 2016/0202335 A1* | 7/2016 | Fielden ................ G01R 33/565 324/309 |
| 2018/0143275 A1* | 5/2018 | Sofka .................. G06K 9/6274 |
| 2018/0143281 A1* | 5/2018 | Sofka .................. G06T 7/0016 |

FOREIGN PATENT DOCUMENTS

| | | |
|---|---|---|
| WO | 2013023214 A1 | 2/2013 |
| WO | 2016004423 A1 | 1/2016 |

OTHER PUBLICATIONS

Alsop, D.C., et al., 1996. "Reduced Transit-Time Sensitivity in Noninvasive Magnetic Resonance Imaging of Human Cerebral Blood Flow." J. Cereb. Blood Flow Metab. 16, pp. 1236-1249.

Alsop, D.C., et al., 2014. "Recommended Implementation of Arterial Spin-Labeled Perfusion MRI for Clinical Applications: A Consensus of the ISMRM Perfusion Study Group and the European Consortium for ASL in Dementia." Magn. Reson. Med. 73, pp. 1-15.

Ashburner, J., et al., 2005. "Unified Segmentation." NeuroImage vol. 26, pp. 839-851.

Asllani, I., et al., 2009. "Separating Function From Structure in Perfusion Imaging of the Aging Brain." Human Brain Mapping vol. 30, pp. 2927-2935.

Bibic, A., et al., 2010. "Denoising of Arterial Spin Labeling Data: Wavelet-Domain Filtering Compared with Gaussian Smoothing." Magn. Reson. Mater. Physics, Biol. Med. vol. 23, pp. 125-137.

Borogovac, A., et al., 2012. Arterial Spin Labeling (ASL) fMRI: Advantages, Theoretical Constrains and Experimental Challenges in Neurosciences. Int. J. Biomed. Imaging vol. 2012, Article 818456, 13 pages.

Buxton, R.B., et al., 1998. "A General Kinetic Model for Quantitative Perfusion Imaging With Arterial Spin Labeling." Magn. Reson. Med. vol. 40, pp. 383-396.

Calamante, F., 2013. "Arterial Input Function in Perfusion MRI: A Comprehensive Review." Prog. Nucl. Magn. Reson. Spectrosc. vol. 74, pp. 1-32.

Chappell, M.A., et al., 2011. "Partial Volume Correction of Multiple Inversion Time Arterial Spin Labeling MRI Data." Magn. Reson. Med. vol. 65, pp. 1173-1183.

Chappell, M.A., et al., 2009. "Variational Bayesian Inference for a Nonlinear Forward Model." IEEE Trans. Signal Process. vol. 57, pp. 223-236.

Dai, W., et al., 2008. "Continuous Flow-Driven Inversion for Arterial Spin Labeling Using Pulsed Radio Frequency and Gradient Fields." Magn. Reson. Med. vol. 60, pp. 1488-1497.

Dai, W., et al., 2012. "Reduced Resolution Transit Delay Prescan for Quantitative Continuous Arterial Spin Labeling Perfusion Imaging." Magn. Reson. Med. vol. 67, pp. 1252-1265.

Dai, W., et al., 2010. "Modified Pulsed Continuous Arterial Spin Labeling for Labeling of a Single Artery." Magn. Reson. Med. vol. 64, pp. 975-982.

Dai, W., et al., 2013. "Volumetric Measurement of Perfusion and Arterial Transit Delay Using Hadamard Encoded Continuous Arterial Spin Labeling." Magn. Reson. Med. vol. 69, pp. 1014-1022.

Detre, J. A., et al., 2002. "Technical Aspects and Utility of fMRI Using BOLD and ASL." Clin. Neurophysiol. vol. 113, pp. 621-634.

Detre, J. A., et al., 1992. "Perfusion Imaging." Magn. Reson. Med. vol. 23, pp. 37-45.

Duhamel, G., et al., 2003. "Evaluation of Systematic Quantification Errors in Velocity-Selective Arterial Spin Labeling of the Brain." Magn. Reson. Med. vol. 50, pp. 145-153.

Fielden, S.W., et al., 2011. "Variable-Flip Angle 3D-Turbo Spin Echo Imaging Utilizing Spiral Acquisitions." Proc. Intl. Soc. Mag. Reson. Med. vol. 19, p. 2820.

Fielden, S.W., et al., 2014. "Noncontrast Peripheral MRA with Spiral Echo Train Imaging." Magn. Reson. Med., 8 pages.

Garcia, D.M., et al., 2005. "Efficiency of Inversion Pulses for Background Suppressed Arterial Spin Labeling." Magn. Reson. Med. vol. 54, pp. 366-372.

Guerquin-Kern, M., et al., 2012. "Realistic Analytical Phantoms for Parallel Magnetic Resonance Imaging." IEEE Trans. Med. Imaging vol. 31, No. 3, pp. 626-636.

Hasebroock, K.M., et al., 2009. "Toxicity of MRI and CT Contrast Agents." Expert Opin. Drug Metab. Toxicol. vol. 5, No. 4, pp. 403-416.

Huang, C., et al., 2012. "T2 Mapping From Highly Undersampled Data by Reconstruction of Principal Component Coefficient Maps Using Compressed Sensing." Magn. Reson. Med. vol. 67, pp. 1355-1366.

Lingala, S.G., et al., 2011. "Accelerated Dynamic MRI Exploiting Sparsity and Low-Rank Structure: k-t SLR." IEEE Trans. Med. Imaging, vol. 30, No. 5, pp. 1042-1054.

Lu, H., et al., 2004. "Determining the Longitudinal Relaxation Time (T1) of Blood at 3.0 Tesla." Mag. Reson. Med. vol. 52, pp. 679-682.

Lustig, M., et al., 2007. "Sparse MRI: The Application of Compressed Sensing for Rapid MR Imaging." Magn. Reson. Med. vol. 58, pp. 1182-1195.

Lustig, M., et al., 2010. "SPIRiT: Iterative Self-Consistent Parallel Imaging Reconstruction From Arbitrary k-Space." Magn. Reson. Med. vol. 64, pp. 457-471.

Macintosh, B.J., et al., 2012. "Hemodynamic Alterations in Vertebrobasilar Large Artery Disease Assessed by Arterial Spin-Labeling MR Imaging." AJNR. Am. J. Neuroradiol. vol. 33, pp. 1939-1944.

Maleki, N., et al., 2011. "Optimization of Background Suppression for Arterial Spin Labeling Perfusion Imaging." Magn. Reson. Mater Phy., vol. 25, pp. 127-133.

Meyer, C.H., et al., 2011. "Dual-Density and Parallel Spiral ASL for Motion Artifact Reduction." Proc. Intl. Soc. Mag. Reson. Med. vol. 19, p. 3986.

Mugler, J.P., 2014. "Optimized Three-Dimensional Fast-Spin-Echo MRI." J. Magn. Reson. Imaging. pp. 1-22.

Murphy, M., et al., 2012. "Fast 1-SPIRiT Compressed Sensing Parallel Imaging MRI: Scalable Parallel Implementation and Clinically Feasible Runtime." IEEE Trans. Med. Imaging vol. 31, No. 6, pp. 1250-1262.

Petersen, E.T., et al., 2006. "Model-Free Arterial Spin Labeling Quantification Approach for Perfusion MRI." Magn. Reson. Med. vol. 55, pp. 219-232.

(56) References Cited

OTHER PUBLICATIONS

Qiu, M., et al., 2010. "Arterial Transit Time Effects in Pulsed Arterial Spin Labeling CBF Mapping: Insight From a PET and MR Study in Normal Human Subjects." Magn. Reson. Med. vol. 63, pp. 374-384.

Rusinek, H., et al., 2010. "Hippocampal Blood Flow in Normal Aging Measured With Arterial Spin Labeling at 3T." Magn. Reson. Med. vol. 65, No. 1, pp. 128-137.

Santos, N., et al., 2011. "Optimal Sampling and Estimation in PASL Perfusion Imaging." IEEE Trans. Biomed. Eng. vol. 58, No. 11, pp. 3165-3174.

Wang, D.J., et al., 2013. "Multi-Delay Multi-Parametric Arterial Spin-Labeled Perfusion MRI in Acute Ischemic Stroke—Comparison with Dynamic Susceptibility Contrast Enhanced Perfusion Imaging." NeuroImage Clin. vol. 3, pp. 1-7.

Wang, D.J., et al., 2012. "The Value of Arterial Spin-Labeled Perfusion Imaging in Acute Ischemic Stroke—Comparision With Dynamic Susceptibility Contrast-Enhanced MRI." vol. 43, pp. 1018-1024.

Wang, Z., et al., 2004. "Image Quality Assessment: From Error Visibility to Structural Similarity." IEEE Trans Image Process. vol. 13, 14 pages.

Wells, J. A., et al., 2010. "Reduction of Errors in ASL Cerebral Perfusion and Arterial Transit Time Maps Using Image De-Noising." Magn. Reson. Med. vol. 64, pp. 715-724.

Wells, J. A., et al., 2010. "In Vivo Hadamard Encoded Continuous Arterial Spin Labeling (H-CASL)." Magn. Reson. Med. vol. 63, pp. 1111-1118.

Wu, W.C., et al., 2007. "A Theoretical and Experimental Investigation of the Tagging Efficiency of Pseudocontinuous Arterial Spin Labeling." Magn. Reson. Med. vol. 58, pp. 1020-1027.

Xie, J., et al., 2008. "Optimal Design of Pulsed Arterial Spin Labeling MRI Experiments." Magn. Reson. Med. vol. 59, pp. 826-834.

Ye, F.Q., et al., 2000. "Noise Reduction in 3D Perfusion Imaging by Attenuating the Static Signal in Arterial Spin Tagging (ASSIST)." Magn. Reson. Med. vol. 44, pp. 92-100.

Yoshiura, T., et al., 2009. "Simultaneous Measurement of Arterial Transit Time, Arterial Blood Volume, and Cerebral Blood Flow Using Arterial Spin-Labeling in Patients with Alzheimer Disease." Am. J. Neuroradiol. vol. 30, pp. 1388-1393.

Zhao, L., et al., 2012. "Accelerated Kinetic ASL Using 3D Spiral TSE and Compressed Sensing." Proc. Intl. Soc. Mag. Reson. Med. vol. 20, p. 1997.

Zhao, L., et al., 2013. "Accelerated 3DPCASL Using Compressed Sensing." Proc. Intl. Soc. Mag. Reson. Med. vol. 21, p. 2157.

Zhao, L., et al., 2013. "Optimal PLD Design and Maximum Likelihood CBF Estimation for Dynamic PCASL With Rician Noise." Proc. Intl. Soc. Mag. Reson. Med. vol. 21, p. 2164.

Zhao, L., et al., 2012. "Optimal Kinetic PASL Design and CBF Estimation With Low SNR and Rician Noise." Proc. Intl. Soc. Mag. Reson. Med. vol. 20, p. 3494.

\* cited by examiner

RAPID 3D DYNAMIC ARTERIAL SPIN LABELING WITH A SPARSE MODEL-BASED IMAGE RECONSTRUCTION

CROSS-REFERENCE TO RELATED APPLICATIONS

This Application claims priority to, and benefit under 35 U.S.C. § 119(e) of, U.S. Provisional Patent Application No. 62/200,943, filed Aug. 4, 2015, and U.S. Provisional Patent Application No. 62/323,394, filed Apr. 15, 2016, which are hereby incorporated by reference herein in their entireties as if fully set forth below.

STATEMENT OF RIGHTS UNDER FEDERALLY-SPONSORED RESEARCH

This invention was made with government support under grant NIH R01 HL079110, awarded by the National Institutes of Health. The government has certain rights in this invention.

BACKGROUND

Arterial spin labeling (ASL) (Detre et al., 1992) is a non-invasive and non-contrast perfusion imaging method for magnetic resonance imaging (MRI). By deriving perfusion data from the natural magnetic resonance (MR) signal of magnetically tagged blood, instead of from an extrinsic contrast agent, ASL provides a safer option for assessing tissue perfusion in patients at risk of nephrogenic systemic fibrosis (Hasebroock and Serkova, 2009) and a preferable option in other situations, such as when imaging infants and children. Cerebral blood flow (CBF) maps estimated using ASL are consistent with dynamic susceptibility contrast (DSC) results and have been widely applied to cerebrovascular studies, such as stroke (Wang et al., 2012) and Alzheimer's disease (Yoshiura et al., 2009). ASL is also preferable for studies requiring repeated perfusion assessments in a short period of time, such as functional MRI (Borogovac and Asllani, 2012; Detre and Wang, 2002). The absolute quantification of blood flow in ASL directly reveals physiological changes (Asllani et al., 2009; Rusinek et al., 2010).

Since the blood magnetization is "labeled" upstream of the volume of interest, a portion of the ASL signal decays before arterial blood flows into the imaging slab, and the acquired signal thus depends on the tagged blood arrival time, called the arterial transit time (ATT), which in turn depends on both the blood flow velocity and the distance between the tagging plane and the imaged region. However, most ASL studies follow the single post label delay (PLD) protocol, which results in a "static" 2D/3D ASL image. It cannot provide a subject-dependent ATT map and requires a simplified ASL model, which may result in errors in CBF quantification (Dai et al., 2012; Qiu et al., 2010). A PLD longer than the ATT can ensure the blood bolus has flowed into surrounding tissue and reduces estimation error (Alsop and Detre, 1996), but this method may miss the peak ASL signal and requires prior knowledge of the ATT.

A multiple-PLD protocol can measure multiple phases of ASL perfusion and fully characterize the ASL dynamic model. It can improve CBF accuracy and provide rich hemodynamic information, such as ATT for characterizing cerebrovascular diseases (Macintosh et al., 2012). But, the intrinsically low signal-to-noise ratio (SNR) of ASL can require extensive signal averaging, and thus a multiple-PLD protocol may become prohibitively time-consuming.

Dynamic ASL imaging can be accelerated in two ways: (1) acquiring undersampled k-space data, and (2) reducing the number of averages. However, accelerating ASL data acquisition in this way comes at the cost of reduced image quality and CBF accuracy using conventional techniques.

It is with respect to these and other considerations that the various embodiments described below are presented.

SUMMARY

Some aspects of the present disclosure relate to systems, methods, and computer-readable media for rapid 3D dynamic ASL with a sparse model-based image reconstruction.

In one aspect, the present disclosure relates to a method which, in one embodiment, includes acquiring magnetic resonance data associated with an area of interest of a subject. The magnetic resonance data includes data associated with arterial spin labeling (ASL) of the area of interest. The method also includes performing image reconstruction on the acquired magnetic resonance data. The image reconstruction includes compressed sensing enforcing a model-based sparsity constraint, where the model-based sparsity constraint is based on an ASL signal prototype dictionary.

In another aspect, the present disclosure relates to a system for dynamic arterial spin labeling (ASL) magnetic resonance imaging (MRI). In one embodiment, the system includes a data acquisition device configured to acquire magnetic resonance data associated with an area of interest of a subject. The magnetic resonance data includes data associated with arterial spin labeling (ASL) of the area of interest. The system also includes one or more processors configured to cause the system to perform functions that include performing image reconstruction on the acquired resonance data. The image reconstruction includes compressed sensing enforcing a model-based sparsity constraint, and the model-based sparsity constraint is based on an ASL signal prototype dictionary.

In yet another aspect, the present disclosure relates to a non-transitory computer-readable medium which, in one embodiment, stores instructions that, when executed by one or more processors, cause a computing device to perform functions that include acquiring magnetic resonance data associated with an area of interest of a subject. The magnetic resonance data includes data associated with arterial spin labeling (ASL) of the area of interest. The functions performed also include image reconstruction performed on the acquired resonance data. The image reconstruction includes compressed sensing enforcing a model-based sparsity constraint, where the model-based sparsity constraint is based on an ASL signal prototype dictionary.

Other aspects and features according to the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale. The patent or application file contains at least one drawing executed in color. Copies of this patent or patent application publication with the color drawing(s) will be provided by the Office upon request and payment of the necessary fee.

Figure 1:
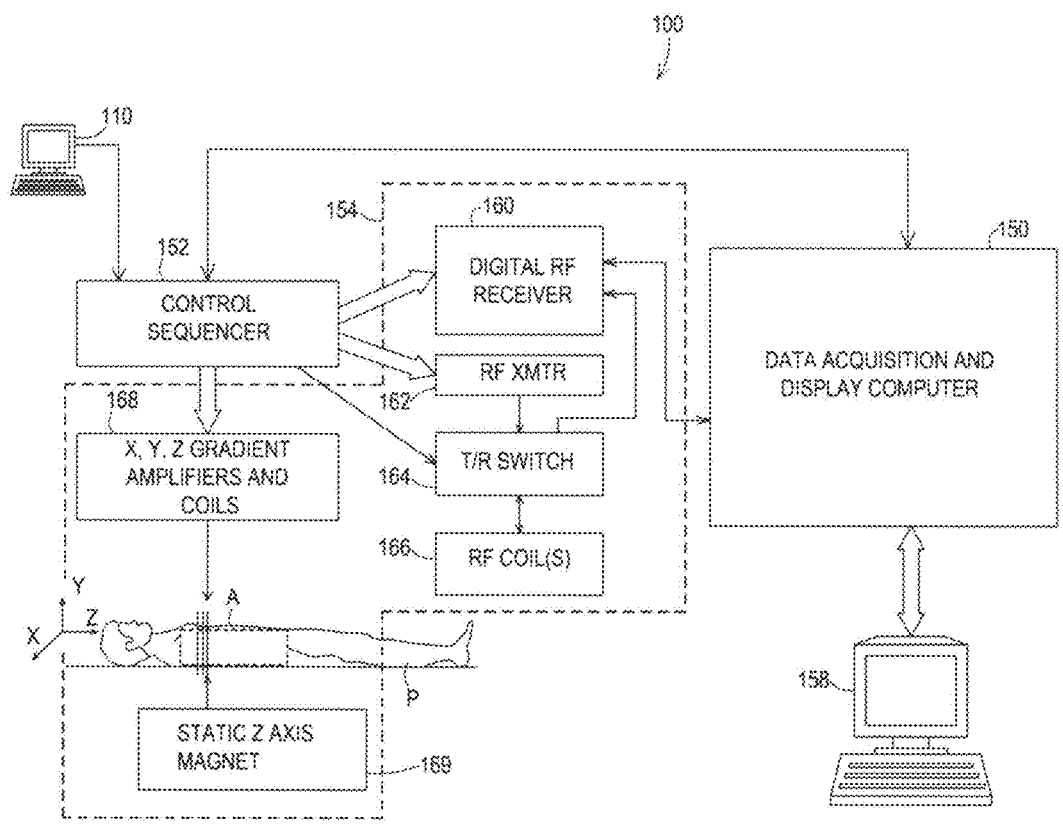
FIG. 1 is a system diagram illustrating an imaging system capable of implementing aspects of the present disclosure in accordance with one or more embodiments.

$e^{-6}$) and 20 s/OT (mean residual=4.3 $e^{-6}$). Units: Dynamic model fitting residual (a.u.); CBF maps (ml/100 g/min); ATT maps (seconds).

DETAILED DESCRIPTION

In some aspects, the present disclosure relates to rapid 3D dynamic ASL with a sparse model-based image reconstruction. In some embodiments, accelerated dynamic ASL with improved SNR and robustness to motion uses model-based image reconstruction that exploits the inherent sparsity of dynamic ASL data. Some embodiments utilize a single-shot 3D turbo spin echo spiral pulse sequence accelerated using a combination of parallel imaging and compressed sensing. In some embodiments, this pulse sequence is incorporated into a dynamic pseudo continuous ASL acquisition acquired at multiple observation times, and the resulting images are jointly reconstructed enforcing a model of potential perfusion time courses.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" (or "patient") may be any applicable human, animal, or other organism, living or dead, or other biological or molecular structure or chemical environment, and may relate to particular components of the subject, for instance specific tissues organs, tissues, or fluids of a subject (e.g., human tissue in a particular area of the body of a living subject), which may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. All references cited and discussed in this specification are incorporated herein by reference in their entireties and to the same extent as if each reference was individually incorporated by reference.

A detailed description of aspects of the present disclosure will now be provided with reference to the accompanying drawings. The drawings form a part hereof and show, by way of illustration, specific embodiments or examples. In referring to the drawings, like numerals represent like elements throughout the several figures.

FIG. 1 is a system diagram illustrating an operating environment capable of implementing aspects of the present disclosure in accordance with one or more example embodiments. FIG. 1 illustrates an example of a magnetic resonance imaging (MRI) system 100, including a data acquisition and display computer 150 coupled to an operator console 110, an MRI real-time control sequencer 152, and an MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a subject P to be imaged, for example to implement magnetic resonance imaging sequences in accordance with various embodiments of the present disclosure. A contrast-enhanced image of an area of interest A of the subject P (which may also be referred to herein as a "region of interest") may be shown on display 158. The display 158 may be implemented through a variety of output interfaces, including a monitor, printer, or data storage.

The area of interest A corresponds to a region associated with one or more physiological activities in subject P. The area of interest shown in the example embodiment of FIG. 1 corresponds to a chest region of subject P, but it should be appreciated that the area of interest for purposes of implementing various aspects of the disclosure presented herein is not limited to the chest area. It should be recognized and appreciated that the area of interest in various embodiments may encompass various areas of subject P associated with various physiological characteristics, such as, but not limited to the brain region, heart region, upper or lower extremities, or other organs or tissues. Physiological activities that may be evaluated by methods and systems in accordance with various embodiments of the present disclosure may include, but are not limited to, fluid flow such as blood flow, muscle movement, organ function, or other conditions.

It should be appreciated that any number and type of computer-based medical imaging systems or components, including various types of commercially available medical imaging systems and components, may be used to practice certain aspects of the present disclosure. Systems as described herein with respect to example embodiments are not intended to be specifically limited to magnetic resonance imaging (MRI) implementations or the particular system shown in FIG. 1.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Figure 2:
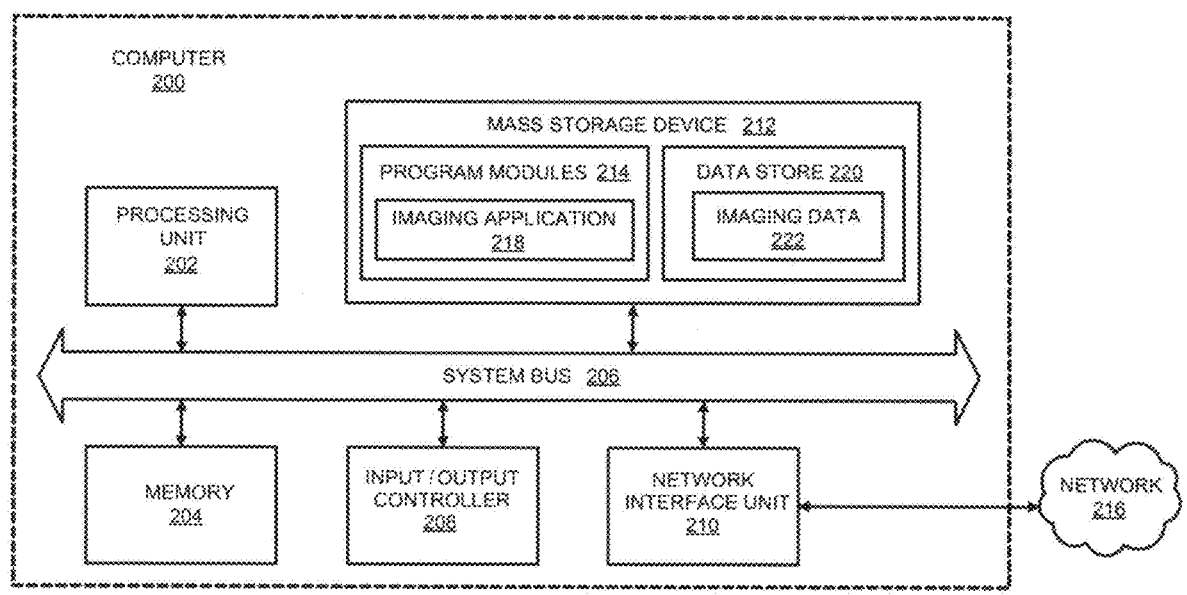
FIG. 2 is a computer architecture diagram showing a general computing system capable of implementing aspects of the present disclosure in accordance with one or more embodiments.
Figure 3:
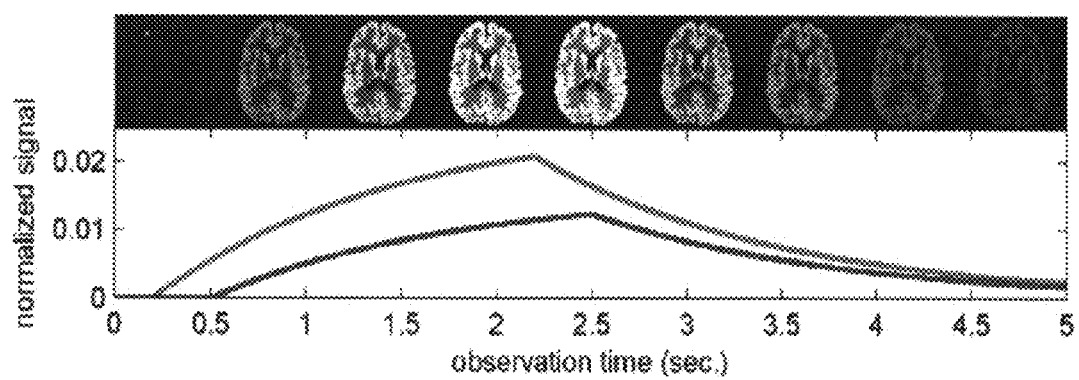
FIG. 3 illustrates evolution of dynamic ASL signals in a numerical phantom. The signal from an individual pixel is temporally slowly varying. The dynamic signals in different pixels (blue and red) follow the same nonlinear perfusion model with different parameter values.

FIG. 2 is a computer architecture diagram showing a general computing system capable of implementing aspects of the present disclosure in accordance with one or more embodiments described herein. A computer 200 may be configured to perform one or more functions associated with embodiments illustrated in one or more of FIGS. 3-15. For example, the computer 200 may be configured to perform aspects described herein for implementing magnetic resonance data acquisition and model-based image reconstruction. It should be appreciated that the computer 200 may be implemented within a single computing device or a computing system formed with multiple connected computing devices. The computer 200 may be configured to perform various distributed computing tasks, in which processing and/or storage resources may be distributed among the multiple devices. The data acquisition and display computer 150 and/or operator console 110 of the system shown in FIG. 1 may include one or more systems and components of the computer 200.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform associated with embodiments illustrated in one or more of FIGS. 3-15 discussed below. The program modules 214 may include an imaging application 218 for performing data acquisition and/or processing functions as described herein, for example to acquire and/or process image data corresponding to magnetic resonance imaging of an area of interest. The computer 200 can include a data store 220 for storing data that may include imaging-related data 222 such as acquired data from the implementation of magnetic resonance imaging in accordance with various embodiments of the present disclosure.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. "Computer storage media", "computer-readable storage medium" or "computer-readable storage media" as described herein do not include transitory signals.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems. The computer 200 may also include an input/output controller 208 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 200. The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology.

The computer storage media may also represent secondary storage, whether implemented as hard drives or otherwise. Hard drive implementations may be characterized as solid state, or may include rotating media storing magnetically-encoded information. The program modules 214, which include the imaging application 218, may include instructions that, when loaded into the processing unit 202 and executed, cause the computer 200 to provide functions associated with one or more embodiments illustrated in FIGS. 3-15. The program modules 214 may also provide various tools or techniques by which the computer 200 may participate within the overall systems or operating environments using the components, flows, and data structures discussed throughout this description.

In general, the program modules 214 may, when loaded into the processing unit 202 and executed, transform the processing unit 202 and the overall computer 200 from a general-purpose computing system into a special-purpose computing system. The processing unit 202 may be constructed from any number of transistors or other discrete circuit elements, which may individually or collectively assume any number of states. More specifically, the processing unit 202 may operate as a finite-state machine, in response to executable instructions contained within the program modules 214. These computer-executable instructions may transform the processing unit 202 by specifying how the processing unit 202 transitions between states, thereby transforming the transistors or other discrete hardware elements constituting the processing unit 202. Encoding the program modules 214 may also transform the physical structure of the computer-storage media. The specific transformation of physical structure may depend on various factors, in different implementations of this description. Examples of such factors may include, but are not limited to the technology used to implement the computer-storage media, whether the computer storage media are characterized as primary or secondary storage, and the like. For example, if the computer storage media are implemented as semiconductor-based memory, the program modules 214 may transform the physical state of the semiconductor memory, when the software is encoded therein. For example, the program modules 214 may transform the state of transistors, capacitors, or other discrete circuit elements constituting the semiconductor memory.

As another example, the computer storage media may be implemented using magnetic or optical technology. In such implementations, the program modules 214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

Further details of certain embodiments of the present disclosure will now be discussed. The following describes some embodiments of the present disclosure for accelerating dynamic ASL imaging, which maintains the image quality and provides accurate and robust parameter quantification. In some embodiments, a rapid and efficient data acquisition method is used: single-shot 3D turbo spin echo (TSE) imaging with a spiral k-space trajectory. However, it should be appreciated that other readouts can be used, such as 3D GRASE (Wang et al., 2013). Spiral TSE parallel imaging is a very rapid imaging method, enabling rapid 3D scanning. In some embodiments, a dual-density spiral trajectory and non-Cartesian parallel imaging are incorporated, which enable single-shot 3D scanning with the desired spatial resolution. Single-shot scanning saves time and is more robust to motion and physiological variations than interleaved scanning. With a dual-density trajectory design, certain methods in accordance with some embodiments of the present disclosure can also be less vulnerable to T2-blurring and susceptibility artifacts, compared to conventional single shot constant-density spiral scanning, which can require a long readout to achieve spatial coverage and resolution (Meyer et al., 2011). However, there is an SNR penalty at high acceleration rates using parallel imaging. In some embodiments of the present disclosure, compressed sensing (Lustig et al., 2007) is also used, which exploits sparsity of the data and grew out of earlier research in nonlinear denoising methods. Compressed sensing can recover the ASL signal from an acquisition with under-sampled k-space and fewer averages. Thus, it is an intriguing option for accelerated ASL image reconstruction (Zhao et al., 2012, 2013). In some embodiments of the present disclosure, a 3D single-shot stack-of-spirals k-space trajectory, parallel imaging, and compressed sensing are combined for highly accelerated image acquisition with excellent SNR.

For dynamic ASL, high acceleration and high SNR are needed, not only for the perfusion images, but also for the resulting parameter maps. In accordance with some embodiments of the present disclosure, a first step in applying compressed sensing to ASL image reconstruction is to enforce a spatial sparsity constraint. This is a promising technique in its own right, and can be used to accelerate ASL image acquisition for each time point separately. Related research into spatial constraints include methods to improve ASL image quality using spatial filters, wavelet sparsity (Bibic et al., 2010) and independent component analysis (Wells et al., 2010). Fortunately, the dynamic ASL problem is even richer with opportunities for compressed sensing.

In some embodiments of the present disclosure, for dynamic ASL perfusion imaging, the similar spatial structure of images at different delay times and prior information about their temporal evolution can be exploited to improve image quality and perfusion parameter estimation. By using the sparsity of dynamic ASL perfusion images in the domain of a perfusion model, the relationship between different time frames can be efficiently used, not just reconstructing each frame separately. The resulting image reconstruction can suppress both random noise and artifacts, because they do not conform to the underlying perfusion model. Implementing some embodiments of the present disclosure results in rapid and robust dynamic ASL imaging, as will be further described below.

The following discussion of various aspects and embodiments of the present disclosure includes descriptions of example implementations and corresponding results. Some experimental data are presented herein for purposes of illustration and should not be construed as limiting the scope of the present disclosure in any way or excluding any alternative or additional embodiments.

Methods

In dynamic ASL, perfusion images with the same CBF information are measured at multiple observation times (OTs). These measurements are conventionally reconstructed separately. But, they can be reconstructed more efficiently by combining all of the dynamic frames with an ASL dynamic model.

Dictionary Representation

Compressed sensing recovers images from noise or noise-like artifacts using a sparsity-promoting image reconstruction. This constrained optimization problem is usually solved by introducing Lagrange multipliers:

$$\hat{x} = \arg\min_x \|Fx - y\|_2 + \lambda \|R(x)\|_p \quad (1)$$

where x is the target image and y is the acquired data. F is a Fourier transform operator that includes the k-space sampling trajectory and under-sampling pattern. R(x) is the representation of x in the sparse transform domain, constrained in the minimization with norm p. λ is a regularization parameter.

The signal x can be represented by a linear combination of a few elements in the dictionary D, which contains n prototypes, $D = \{d_1, d_2, \ldots, d_n\}$:

$$x = \sum_{i=1}^{n} s_i d_i + \epsilon \quad (2)$$

where ϵ is the error tolerance, which limits the sparsity of the representation. $S_i$ is the coefficient of prototype $d_i$ and is an element of a sparse coefficient vector $s = \{s_1, s_2, \ldots, s_n\}$, where most elements are zeros. Compressed sensing improves image quality by enforcing the sparsity of s, while maintaining data fidelity:

$$\hat{x} = \arg\min_x \|Fx-y\|_2 + \lambda\|s\|_p \quad (3)$$

Additional sparsity constraints can be used to improve image quality. The total variation (TV) constraint is commonly used for noise suppression and image recovery. Based on an assumption that the object is piece-wise smooth, TV suppresses noise-like artifacts and maintains edge structure. With this additional constraint, the cost function becomes:

$$\hat{x} = \arg\min_x \|Fx-y\|_2 + \lambda_1\|s\|_{p1} + \lambda_2\|TV(x)\|_{p2} \quad (4)$$

ASL Model and Over-complete Dictionary

K-SVD (Aharon et al., 2006) is an algorithm for generating an over-complete dictionary D, which contains more prototypes than the dimension of the signal x. Compared with an orthogonal dictionary, such as one obtained by principle component analysis (PCA) (Huang et al., 2012), an over-complete dictionary leads to a sparser representation of the signal and improves compressed sensing performance on a signal of limited dimension, such as dynamic ASL, where only a few OT encoding steps are present because of the limited scan time. The K-SVD algorithm builds up the signal prototype dictionary iteratively from a training data set. Because each tissue pixel will follow a valid ASL signal evolution pattern (FIG. 3), it can be described by prototypes based on the ASL dynamic model. Therefore, in accordance with some embodiments of the present disclosure, the K-SVD dictionary was trained with a synthetic dataset generated from an ASL signal model. By using a large number of signal prototypes representing the realistic range of possible ASL parameters, any expected signal can be represented. The K-SVD algorithm then distills the representation down to a smaller dictionary that can still represent any expected signal accurately as a linear combination of a small number of signal prototypes.

In some embodiments, the following single-compartment perfusion model (Buxton et al., 1998; Dai et al., 2012) was used to generated the training data:

$$\Delta M(t) = 2M_0 \alpha f T_1 \exp\left(-\frac{\Delta t}{T_{1,b}}\right) Q(t) \quad (5)$$

$$Q(t) = \begin{cases} 0 & 0 < t < \Delta t \\ 1 - \exp\left(-\frac{t - \Delta t}{T_1}\right) & \Delta t \leq t \leq \Delta t + \tau \\ \exp\left(-\frac{t - \tau - \Delta t}{T_1}\right) - \exp\left(-\frac{t - \Delta t}{T_1}\right) & \Delta t + \tau \leq t \end{cases} \quad (6)$$

where ΔM is the dynamic ASL signal.

When generating the training data, it was assumed that α, the labeling efficiency, is 0.9; $T_1$, the longitudinal relaxation time of brain tissue, is 1500 ms (Alsop et al., 2015); and $T_{1,b}$, the longitudinal relaxation time of blood, is 1660 ms (Lu et al., 2004). $M_0$, the equilibrium magnetization of blood, was normalized to 1. Observation times t and blood bolus duration τ were set to the values used in the dynamic ASL experiment. To cover a range of possible acquired signals, the training data included 9600 ASL dynamic signals with CBF (f) 1-120 ml/100 g/min and ATT (Δt) 50-4000 ms. The K-SVD algorithm generated 256 prototypes.

Compressed Sensing Solver

Figure 4:
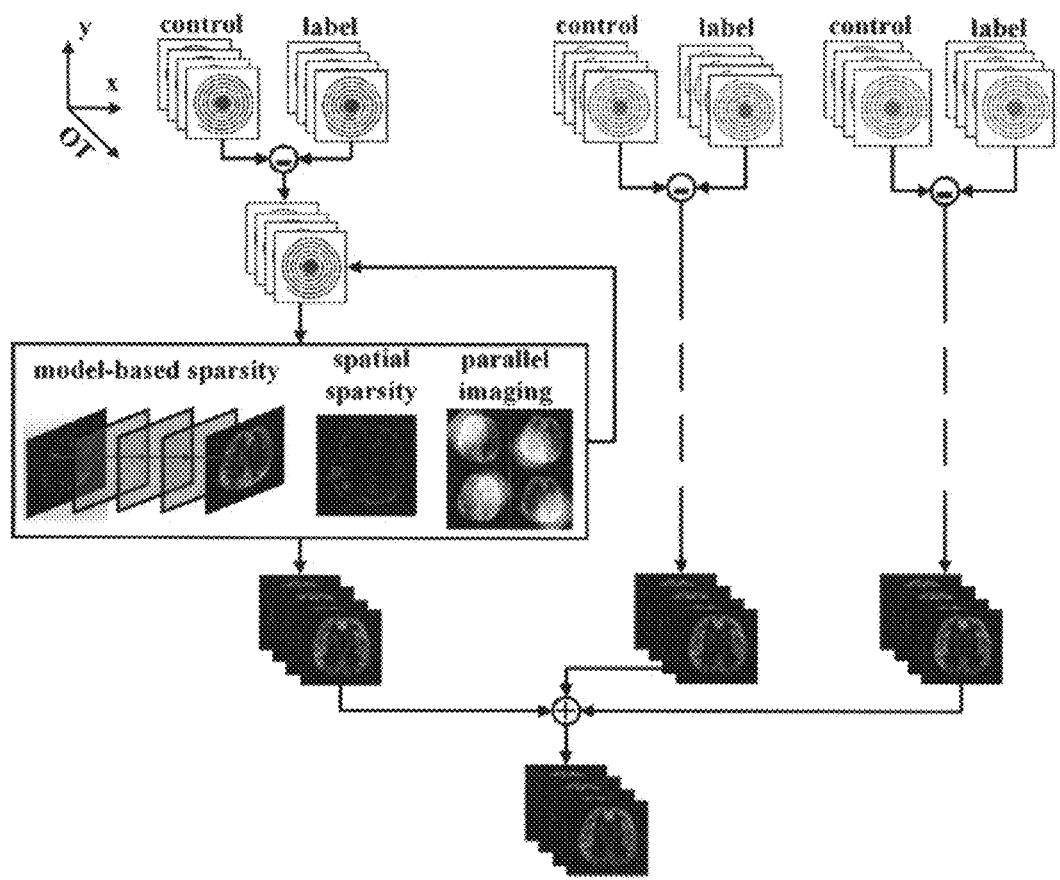
FIG. 4 illustrates an overview of model-based reconstruction in accordance with some embodiments of the present disclosure. As shown, acquired data corresponding to each spiral interleaf are processed separately. Each label image dataset is subtracted from the corresponding control image dataset to generate k-space data with ASL contrast. The ASL images are recovered in a model-based iterative reconstruction by pursuing model-based sparsity, spatial sparsity, and data consistency across multiple-channel measurements.
Figure 5:
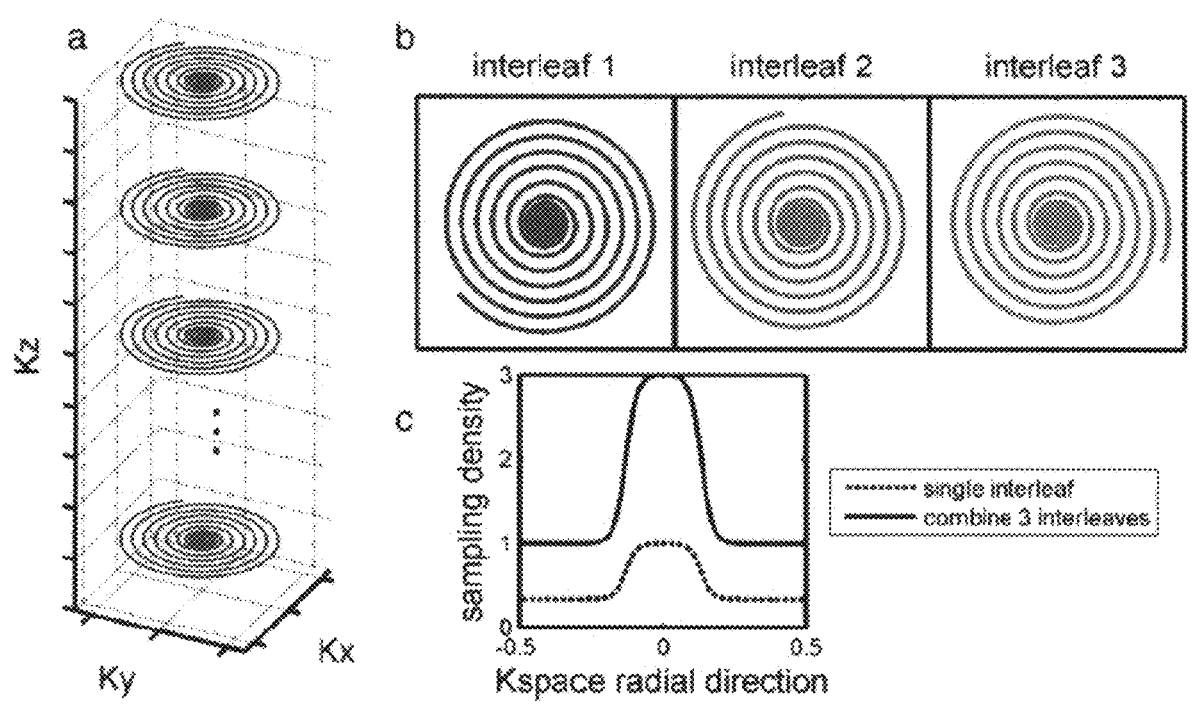
FIG. 5 illustrates a dual-density 3D spiral k-space trajectory. In this 3D spiral TSE pulse sequence, each echo train samples a particular spiral interleaf while the z direction is encoded with a centric view order (a). Each dual-density spiral interleaf fully samples the center of k-space (dashed line in c), providing auto-calibration data for parallel image reconstruction. With different initial spiral angles (b), multiple interleaves can be combined into an oversampled k-space (solid line in c) and reconstructed by a simple gridding method for comparison with accelerated image reconstruction methods.

This image reconstruction problem is a nonlinear optimization problem. In accordance with some embodiments of the present disclosure, the following four steps are applied to solve this problem, as shown in FIG. 4:

1) Define x as the ASL perfusion-weighted image. The complex k-space data is subtracted pair-wise to get the data y with ASL contrast, and x0 is initialized by gridding and zero padding.
2) The multi-OT ASL images are projected onto the pre-trained dictionary D pixel by pixel. Orthogonal matching pursuit is used to enforce sparsity in the over-complete dictionary.

$$\text{minimize } \|s\|_0 \quad (7)$$
$$\text{subject to } \|x - sD\| < \epsilon$$

Q represents an image with sparsity enforced in the domain of the model-based dictionary:

$$Q = sD \quad (8)$$

3) The TV constraint is enforced by a shrinkage with a penalty method (Lingala et al., 2011).

$$P = \frac{TV(x)}{\Sigma\|TV(x)\|_2} \max\left(\Sigma\|TV(x)\|_2 - \frac{\lambda_2}{\beta}, 0\right) \quad (9)$$

4) A least-square function is solved by the conjugate gradient method to maintain data fidelity and enforce the constraints of model-based sparsity Q and total variation P.

$$\hat{x} = \arg\min_x \|Fx-y\|_2 + \lambda_1\|x-Q\|_2 + \lambda_2\|TV(x)-P\|_{p2} \quad (10)$$

If in-plane k-space is undersampled for acceleration, the image can be recovered by using information from multiple channels. SPIRiT (Lustig and Pauly, 2010) is an autocalibrated parallel reconstruction method that can be used with non-Cartesian trajectories. When using undersampled k-space, the calibration consistency penalty and data fidelity terms are combined:

$$\hat{x} = \arg\min_x \|Fx-y\|_2 + \lambda_1\|x-Q\|_2 + \lambda_2\|TV(x)-P\|_2 + \lambda_3\|(G-1)x\|_2 \quad (11)$$

where G is the SPIRiT calibration kernel.

Steps 2-4 are repeated until the stopping criterion (improvement of cost function is less than 0.01% or maximum number of iterations) is satisfied.

Pulse-sequence Design

Blood Tagging

In accordance with some embodiments of the present disclosure, pseudo continuous arterial spin labeling (pCASL) (Dai et al., 2008) was used to tag and build the blood bolus. It achieves flow-driven inversion by repeating small flip angle RF pulses and gradients. The RF pulse train was built by repeating Hanning pulses of 500 μs duration with a 500 μs gap between them. The mean B1 amplitude was 1.63 μT, the slice-selective gradient amplitude was 5 mT/m, and the mean gradient amplitude was 0.2 mT/m, corresponding to nb=7% (Wu et al., 2007). Control and label scans were switched by controlling the phase of RF pulses. The tagging plane was placed 80 mm below the anterior commissure-posterior commissure line.

Background Suppression

In accordance with some embodiments of the present disclosure, background suppression was used in some experiments to reduce background artifacts and stabilize images (Dai et al., 2010; Maleki et al., 2011; Ye et al., 2000). A slab-selective saturation RF pulse with duration 10 ms was applied before the pCASL tagging pulse train. Two nonselective hyperbolic secant inversion pulses with duration 10 ms were applied after the pCASL tagging pulses and before data acquisition. The intervals between background suppression RF pulses were pre-calculated to minimize the maximum residual signal in white matter, gray matter, blood and CSF, with T1=1000, 1500, 1660 and 4200 ms at 3T, respectively.

Vessel Suppression

In accordance with some embodiments of the present disclosure, adiabatic BIR-4 preparation pulses were used to suppress the vascular blood signal, because the intravascular signal often manifests as a bright spot in subtracted perfusion images and can result in over-estimation of CBF. To reduce the RF pulse duration and $T_2$ weighting, a single lobe crusher was used with gradient amplitude 22 mT/m, duration 5000 μs, and rise time 440 μs. For laminar blood flow, the maximum vessel velocity is 1.5 cm/s at the first zero-crossing of the attenuated sinc function (Duhamel et al., 2003).

Imaging Data

In accordance with some embodiments of the present disclosure, k-space data were collected with a stack-of-spirals trajectory using a 3D turbo spin echo (TSE) pulse sequence (Dai et al., 2008; Fielden et al., 2014). In-plane spiral readout gradients were inserted between hard RF refocusing pulses and phase encoding along the slice direction was performed centrically (FIG. 5a). Each echo in a particular TSE echo train collected the same spiral interleaf, with a collection of through-plane phase encodings sampled during the echo train. RF chopping between averages was used to achieve a better slab selection profile by rotating the phase of refocusing RFs by 180 degrees on even averages (Mugler, 2014). Two dummy scans were performed before ASL data collection to build up the steady state for the background signal.

Single-shot Parallel Imaging

In accordance with some embodiments of the present disclosure, parallel imaging was used to accelerate ASL imaging by exploiting redundant information among multiple receiver channels. A dual-density spiral trajectory was used to acquire k-space, with Nyquist sampling during the first ¼ of the readout and under-sampling by a factor of 3 during the rest of the readout. The dual-density design covers a larger k-space area than a Nyquist sampled constant-density spiral with similar readout length. Therefore, it enables single-shot imaging, reduces scan time, and improves motion robustness.

By rotating the spirals, multiple dual-density spirals can be combined to form an oversampled k-space (FIG. 5b and FIG. 5c). This data can be reconstructed by gridding in k-space, yielding a reference image reconstructed using a standard method. This reference image is similar to a conventional multiple-shot spiral scan and it will be compared, as discussed below, to reconstruction using parallel imaging and compressed sensing methods.

Simulations

In accordance with some embodiments of the present disclosure, to demonstrate the performance of compressed sensing with a model-based constraint, a numerical phantom was used to mimic dynamic ASL imaging and CBF estimation. A high resolution T1 weighted image was segmented based on tissue probability maps (Ashburner and Friston, 2005) with published software SPM12. White matter (WM) and grey matter (GM) ROIs were selected and their CBFs were assumed to be 20 and 50 ml/100 g/min, respectively. This simulated CBF map was smoothed by a Gaussian kernel to provide a more realistic transition between tissues and to reduce the spatial resolution. The dynamic perfusion signal of each pixel was generated based on the local CBF value and calculated by the ASL dynamic model outlined above. Nine perfusion images were simulated at OT=600, 1100, 1600, 2100, 2600, 3100, 3600, 4100 and 4600 ms. Other parameters were chosen as follows: normalized equilibrium blood signal $M_0$=1, tissue blood partition coefficient λ=0.9, tissue $T_1$=1500 ms, blood $T_{1,b}$=1660 ms, tagged bolus duration τ=2000 ms.

The noiseless dynamic ASL images were projected onto the trained dictionary, so as to verify the accuracy and sparsity of the model-based dictionary. For noisy ASL images, it was predicted that the signal could be recovered by enforcing its sparsity on the dictionary. This was tested by representing the noisy dynamic ASL images with only a few significant dictionary coefficients.

To test the performance of the model-based constraint with modest random variation of the object, an acquisition with random head motion was simulated. At OT=3600 ms, the control images were independently translated in both the x and y directions by a random distance between −10 and 10 mm in 5% of the repetitions. Independently, 5% of label images were subjected to similar motion. Without background suppression, the control and label images have about 100-fold higher signal than the ASL signal. The mismatch between control and label images resulted in edge enhancement in the difference images, which typically dominated image contrast. Images acquired at other OTs were assumed to be motionless.

To verify the noise suppression, Gaussian noise was added, with σ=0.002. The SNR was less than 10 based on the highest signal in all perfusion images and was lower for the early/late OTs and low perfusion regions. These images were transformed to k-space and reconstructed by the compressed sensing method. Spatial sparsity and model-based sparsity have separate effects on image quality. To verify additional improvement by introducing model-based sparsity, ASL images were constructed using spatial sparsity first and the Lagrange multiplier with the best performance was selected. Then, the model-based constraint was added and evaluated. Image structures and artifacts were also evaluated via root mean squared error (RMSE) and structural similarity index (SSIM) (Wang et al., 2004), compared to noiseless and motionless images.

In the simulation, because of the prior knowledge of the phantom structure, the SNR can be quantified more accurately by using the local standard deviation:

$$SNR = \frac{\text{mean}(ROI)}{\text{std}(ROI)}$$

In Vivo Measurements

Healthy volunteers were imaged on a 3 Tesla Siemens Trio scanner (Erlangen, Germany) with a 12-channel head coil receiver array and body coil transmission.

Lower SNR Dynamic ASL Protocol

To study the performance of methods in accordance with some embodiments of the present disclosure, in an accelerated acquisition with associated lower SNR, dynamic ASL with single-shot dual-density spiral trajectories and without background suppression was performed. Six volunteers were imaged with following protocol. For the multiple-OT ASL measurements, single-shot dual-density spiral scanning was used with an in-plane acceleration factor of 2. The spiral readout duration was 6 ms and the FOV was 200 mm, which gave a nominal spatial resolution of 4.5×4.5 mm². The whole brain was covered by 24 slices with thickness 4.5 mm. Four pairs of control and label images were averaged to improve SNR. Three repetitions of the dual-density spiral were performed with different initial spiral angles. TR was 5 s and TE was 22 ms. For each OT measurement, the scan time was about 2 minutes. 9 OT measurements were acquired sequentially with total scan time of about 18 minutes.

To observe the early perfusion signal of a 2000 ms blood bolus, 9 OTs were designed by varying pCASL tagging durations and PLDs (Table 1). The entire bolus will be observed if the Design OT of the first time point is less than the ATT. More general designs related to this method have been reported for Hadamard tagging design (Dai et al., 2013; Wells et al., 2010).

TABLE 1

| Observation Time Design (ms). | | | | | | | | | |
|---|---|---|---|---|---|---|---|---|---|
| BDesign OT | 600 | 1100 | 1600 | 2100 | 2600 | 3100 | 3600 | 4100 | 4600 |
| Bolus | 500 | 1000 | 1500 | 2000 | 2000 | 2000 | 2000 | 2000 | 2000 |
| Sequence PLD | 100 | 100 | 100 | 100 | 600 | 1100 | 1600 | 2100 | 2600 |

To improve CBF estimation, a saturation recovery sequence with the same 3D stack-of-spirals sequence and the same resolution was employed to measure a $T_1$ map. This sequence used two averages and was repeated 5 times with different TRs (1s, 2s, 3s, 4s and 5s) to acquire images with different $T_1$ weighting.

A $T_1$ map was calculated from the saturation recovery scans with multiple TRs. The images from each TR were reconstructed by SPIRiT. The equilibrium magnetization of the brain signal $M_0$ and the $T_1$ map was estimated by minimizing the least squared error of the saturation recovery equation:

$$M_{sat} = M_0 \left(1 - \exp\left(-\frac{TR}{T1}\right)\right) \quad (12)$$

To evaluate the performance of methods in accordance with some embodiments of the present disclosure, volunteer data were also reconstructed by a gridding method and a parallel imaging method with SPIRiT reconstruction. The residual error in CBF calculation and the SNR from the highest perfusion signal measurement were analyzed by the Wilcoxon signed-rank test. Two ROIs were chosen based on the $T_1$ map: white matter (WM) 10-1300 ms and grey matter (GM) 1300-1900 ms. To test the improvement in the CBF map by methods in accordance with some embodiments of the present disclosure, the different reconstruction methods were compared in a low SNR case. Low SNR images were obtained by using ⅓ of the data, where the first repetition of the dual-density spiral acquisition was chosen from the three repetitions. The gridding method, the parallel image reconstruction and methods in accordance with some embodiments of the present disclosure were used to reconstruct the ASL images, which provided the low SNR CBF maps. Because DSC images were not available, the CBF map from all available ASL data was treated as a high SNR gold standard. By comparing the similarity of CBF maps between high SNR and low SNR cases, the performance of reconstruction methods were evaluated and the results were analyzed by the Wilcoxon signed-rank test across six volunteers.

Accelerated Dynamic ASL Protocol

Two additional experiments were performed to demonstrate accelerated dynamic ASL with background suppression, dual-density readouts and model-based image reconstruction in accordance with some embodiments of the present disclosure. The 3D stack-of-spirals trajectory was implemented with single-shot dual-density spirals with 7.2-ms readouts. These slightly longer dual-density readouts provided the same 4×4 mm² in-plane resolution while also providing calibration data necessary for autocalibrated parallel image reconstruction. The FOV was 200 mm and the in-plane resolution was 4×4 mm². 24 slices with thickness 4 mm were acquired. TR was 5.0-5.5 s and TE was 23 ms. Three repetitions of the dual-density spiral trajectory were acquired with different spiral rotation angles. Two averages resulted in scan time of approximately 60 s per OT measurement.

Nine measurements were acquired with OTs=800, 1300, 1800, 2300, 2800, 3300, 3800, 4300 and 4800 ms. To observe the early perfusion signal of a 1800 ms blood bolus, 9 OTs were designed by varying pCASL tagging duration and PLD (Table 2).

TABLE 2

| Observation Time Design (ms) | | | | | | | | | |
|---|---|---|---|---|---|---|---|---|---|
| Design OT | 800 | 1300 | 1800 | 2300 | 2800 | 3300 | 3800 | 4300 | 4800 |
| Bolus Duration | 300 | 800 | 1300 | 1800 | 1800 | 1800 | 1800 | 1800 | 1800 |
| Sequence PLD | 500 | 500 | 500 | 500 | 1000 | 1500 | 2000 | 2500 | 3000 |

To quantify CBF, the equilibrium blood signal $M_0$ was measured by the same sequence at TR=6 s, but without background suppression and flow suppression. To validate the trade-off between acceleration and image quality, data from three repetitions of dual-density spiral scans were processed separately. When all three repetitions were included, ASL images were acquired in 60 s per OT measurement. When two of the three repetitions were used, scan time was 40 s per OT measurement, and when only one repetition was used, scan time reduced to 20 s per OT measurement.

CBF Quantification

ASL images $LM_1$ from multiple observation times OTi were fitted to the dynamic SL model with minimization of the least squared error, resulting in CBF and ATT.

In addition to calculating M-CBF and M-ATT based directly on fitting the images to a perfusion model, other methods were tested for calculating an ATT map and the associated CBF map. The PLD weighted delay method (Dai et al., 2012) is a robust method for calculating ATT. Because there is a monotonic relationship between ATT and averaged dynamic images with PLD weighting, ATT can be reliably obtained using a lookup table of weighted delays without knowledge of CBF. Here a similar generalized weighted delay method was developed based on multi-OT acquisition. The ATT map (W-ATT) is calculated based on the monotonic relationship between ATT and a weighted average of the images:

$$WT = \frac{\sum_{i=1}^{9} OT_i \Delta M_i}{\sum_{i=1}^{9} \Delta M_i}$$

Using the W-ATT, a CBF map was calculated at each OT and averaged to obtain a weighted BF (W-CBF).

Image reconstruction and data analysis were performed in MATLAB 2012b (The MathWorks, Inc.) on a 4× GTX 680 Workstation (Amax Information Technologies, Inc.) with 12 CPUs (Intel Xeon E5-2640 2.50GHz Processor LGA2011).

Results

Simulations

Figure 6:
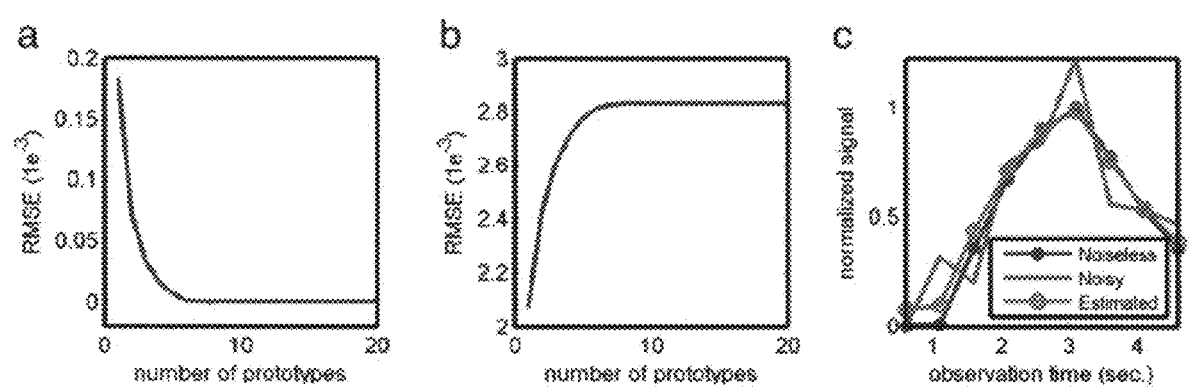
FIG. 6 illustrates aspects of a trained dictionary representing an ASL signal. For noiseless data (a), only a few prototypes are needed to represent the signal with high accuracy. For noisy data (b), image denoising can be performed by projecting the signal onto a few prototypes. One selected ASL pixel illustrates that a dictionary representation can approximate the noiseless signal more accurately than the noisy signal itself (c).

Simulated multi-OT ASL images represented by the overcomplete dictionary and the associated approximation errors are shown in FIG. 6. The noiseless ASL signal was accurately approximated using just a few prototypes in the dictionary (FIG. 6a). More prototypes yielded improved signal approximation but also tend to approximate the noise, because of the low SNR of the ASL signal (FIG. 6b). In FIG. 6c, a noisy ASL signal (RMSE=1.84 $e^{-3}$) was projected onto the dictionary and then represented by a few primary prototypes, which suppresses noise and recovers the signal (RMSE=5.8 $e^{-4}$).

Figure 7:
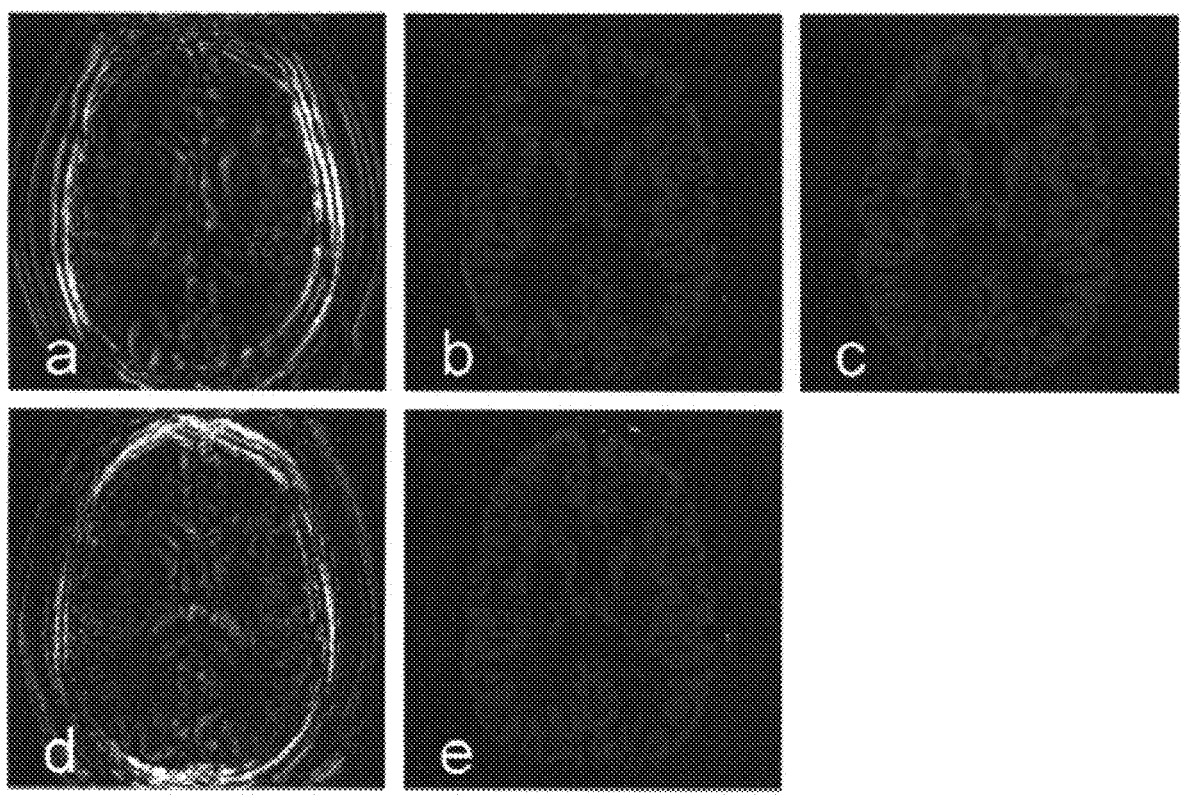
FIG. 7 shows images illustrating that model-based sparsity reduces artifacts in multi-OT ASL images. In the noiseless case, one of the dynamic ASL images contained motion artifacts (a) from subtraction between control and label images. By projecting the multi-OT signal onto the model-based dictionary, the motion artifact was reduced dramatically (b), because its dynamic pattern was distinct from the ASL model. As a reference, the noiseless and artifact-free image is shown in (c). Similar results were seen with noisy data (d, e). All images are windowed the same, demonstrating the magnitude of the motion artifacts.

FIG. 7 shows that the model-based constraint reduced random artifacts. Modest rigid bulk motion resulted in ring-like artifacts around the brain and bright spots in the CSF region, as shown in noiseless ASL (a). Because this random motion artifact did not follow the ASL signal decay model, it was suppressed by the model-based dictionary (b). As a reference, the noiseless and motionless image is shown in (c). Similarly, in noisy data (d), the motion artifact and background noise were suppressed by projecting the dynamic signal onto the dictionary (e). Some motion artifacts remain near the CSF region, because some random noise and motion were dominant in the region with low perfusion signal. Some of these random variations fit the ASL model and thus were represented by the dictionary.

Figure 8:
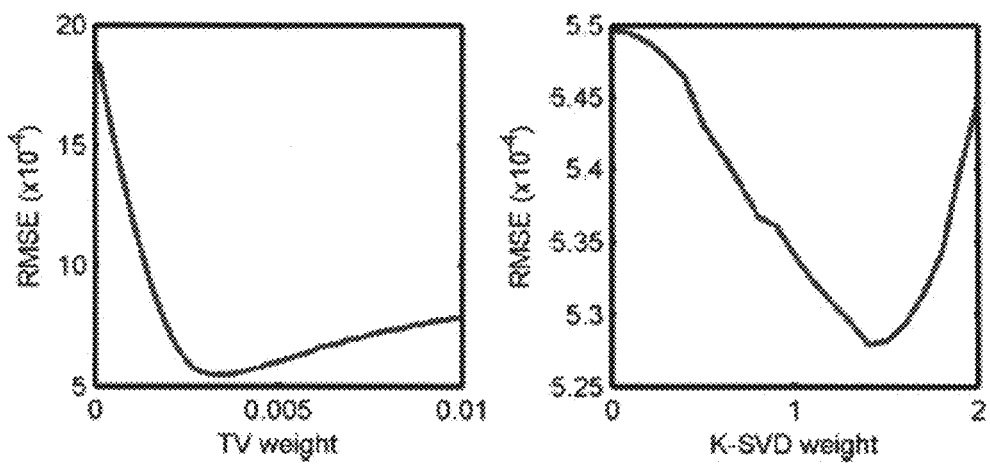
FIG. 8 illustrates regularization parameter searching in compressed sensing. As shown (see left), RMSE changed with spatial TV weights only. By adding the K-SVD constraint, the error is further reduced (see right).

The performance of constrained image reconstruction can depend on the choice of Lagrange multipliers. To demonstrate the image quality improvement achieved by enforcing model-based sparsity, the multipliers were chosen in two steps. First, with a spatial constraint only, the inventors searched for the best TV weight minimizing RMSE. It was an "L-curve" as shown in FIG. 8 (left) and the minimum RMSE was achieved with the TV weight 0.0033. Then, model-based sparsity was performed with images at 9 OTs and combined with this "best" TV. From FIG. 8 (right), the RMSE was further reduced and K-SVD achieved its best performance at weight 1.4.

Figure 9:
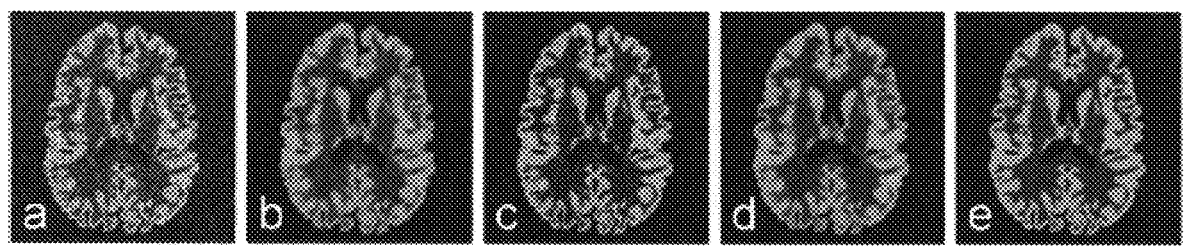
FIG. 9 shows simulated ASL images reconstructed by compressed sensing. The complex Gaussian noise in initial images (a) was suppressed by the compressed sensing reconstruction with spatial TV constraint (b) and model-based sparsity (c). By combining spatial and model-based sparsity, the image quality is improved further (d). The noiseless image (e) is shown for reference.

The above results are more clearly demonstrated in simulated ASL images (FIG. 9). Spatial TV (b) suppressed noise and improved the ASL image SNR. Model-based reconstruction (c) enforced the signal changes in OT encoding space towards the dynamic model and suppressed noise along the OT encoding dimension. The combination of the above two types of sparsity (d) improved the image quality further. Initial noisy (a) and ideal (e) images are also shown for reference.

Quantitation of local SNR and estimation error are shown in Table 3. For all ROIs, the compressed sensing reconstruction increased the SNR and the model-based sparsity improved it further. Compared with the noiseless ASL signal, compressed sensing with spatial TV and model-based K-SVD constraints increased the image similarity, reduced the error from background noise in images by a factor of 3.8, and reduced the residual in perfusion maps by a factor of 2.4.

TABLE 3

Improvement of ASL image quality and CBF maps by compressed sensing.

| | SNR WM | SNR GM | Image SSIM | Image RMSE ($e^{-4}$) | CBF RMSE | CBF fitting residual ($e^{-4}$) |
|---|---|---|---|---|---|---|
| Initial | 3.4 | 6.4 | 0.42 | 20.0 | 8.2 | 61.4 |
| TV | 25.4 | 45.0 | 0.71 | 5.5 | 5.9 | 25.3 |
| Model | 5.7 | 14.0 | 0.55 | 11.7 | 7.1 | 37.5 |
| TV + Model | 27.7 | 52.1 | 0.73 | 5.3 | 5.3 | 25.2 |

Experiments

Figure 10:
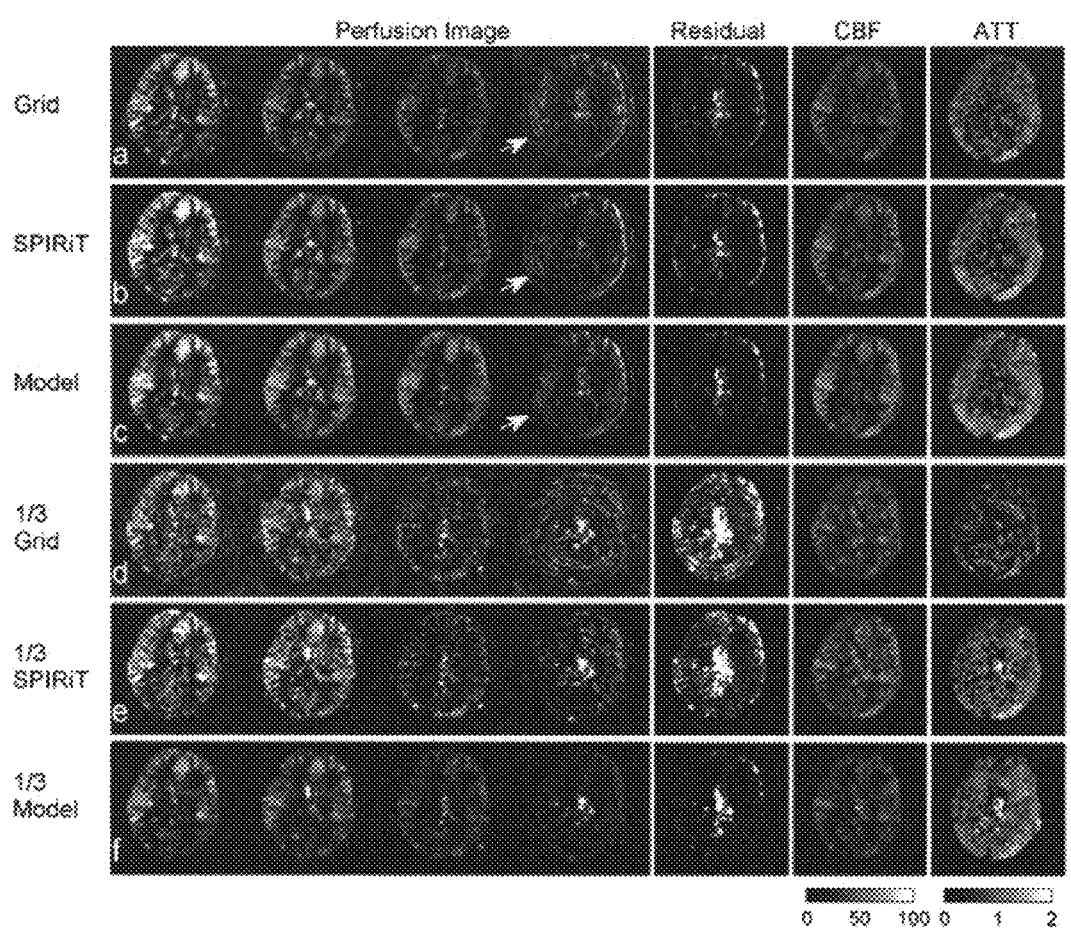
FIG. 10 shows dynamic pCASL perfusion images from selected OTs (2600, 3100, 3600, 4100 ms) in a normal volunteer. The gridding reconstruction (a) shows high motion artifacts and background noise. The SPIRiT reconstruction (b) eliminated many of the artifacts in the gridding reconstruction. The model-based reconstruction suppressed background noise and reduced the estimation error in the CBF (c). As the arrow highlights, the motion artifacts obtained using the gridding method (a) and SPIRiT reconstruction (b) were suppressed when the model-based sparsity constraint was used (c). When using only ⅓ of the acquired data and reducing the scan time to 40s at each OT, the SNR of perfusion images dropped substantially in the Grid (d) and SPIRiT (e) reconstruction and there was more fitting error, as shown by the CBF calculation residual. Again, the proposed method improved the images, reduced the fitting error, and provided a similar CBF map to the high-SNR results (f). Units: Dynamic model fitting residual (a.u.); CBF maps (ml/100 g/min); ATT maps (seconds).

FIG. 10 shows one slice from a dynamic ASL 3D image set acquired with a dual-density spiral trajectory and without background suppression. The conventional non-Cartesian gridding reconstruction (a) resulted in high background noise and motion artifacts. Parallel reconstruction with SPIRiT (b) reduced noise and stabilized the image. As in the simulations, the model-based reconstruction (c) suppressed the noise in the background and improved the SNR of experimental ASL images.

Methods in accordance with the present disclosure also corrected artifacts. As highlighted by the arrows in FIG. 10, the brain had a slight mismatch between control and label measurements, which resulted in ring-like motion artifacts. Because the motion occurred irregularly, the model-based constraint reduced the artifact because it had a poor representation in the model-based dictionary. The model-based constraint can suppress motion at a single OT, because the model information can be provided by images at other OTs. If more of the ASL images artifacts or the artifacts were more severe, the methods in accordance with some embodiments of the present disclosure might fail to detect the perfusion signal.

The CBF maps are shown on the right of FIG. 10. In the residual maps of CBF fitting, methods in accordance with some embodiments of the present disclosure reduced the residual in GM and WM regions, compared with the gridding and parallel image reconstructions. It also reduced the error from CSF, which does not contain perfusion signal, and the edge of brain, which exhibits motion artifacts.

To show the improvement in accuracy of methods in accordance with some embodiments of the present disclosure, the high SNR result from all the acquired data was considered to be a gold standard and compared the CBF map from only one third of acquired data to it, which reduced the total scan time from 18 minutes to about 6 minutes for nine OTs. A conventional gridding reconstruction (d) is not feasible for this data set, because k-space is undersampled and thus the resultant images would suffer from aliasing. The model-based reconstruction (f) was more stable, had higher SNR, and lower fitting error than the parallel image reconstruction (e). The proposed method results in a CBF map that provides a much closer approximation to the high SNR results (a, b, c).

Figure 11:
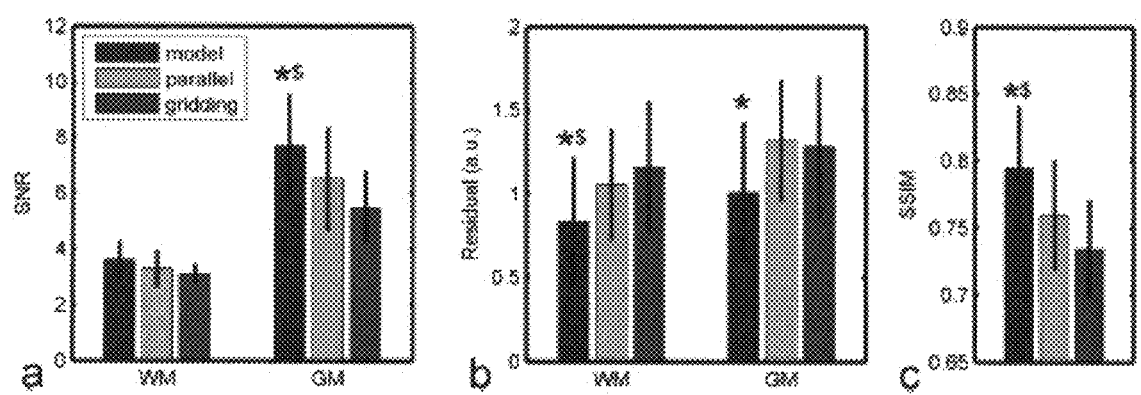
FIG. 11 illustrates ASL image SNR and CBF estimation residual in volunteers (N=6, mean±standard deviation). Regions of interest (ROIs) of grey matter (GM) and white matter (WM) were chosen based on T1 value. Compared with gridding and parallel image reconstruction, image reconstruction in accordance with some embodiments of the present disclosure improved SNR (a) and reduced estimation residuals (b) significantly. With ⅓ of the data, the image reconstruction in accordance with some embodiments of the present disclosure also provided better structural similarity to the high SNR results (c). In the same ROI, * P<0.05 versus the parallel reconstruction method; $ P<0.05 versus the gridding method.

FIG. 11 shows the statistical analysis of the six volunteers' images with the low SNR protocol. FIG. 11a shows SNR improvement using a method in accordance with some embodiments of the present disclosure. In the gray matter region, methods in accordance with some embodiments of the present disclosure significantly improved the SNR (P<0.05) compared with gridding and parallel image reconstruction. FIG. 11b shows the model fitting residual of CBF estimation in the volunteers. Methods in accordance with some embodiments of the present disclosure resulted in less estimation error versus parallel and gridding reconstruction in white matter (P<0.05). Also, significant improvement was achieved in the grey matter compared with parallel imaging. Treating the high SNR CBF map from all available data as a gold standard, the CBF maps from only ⅓ of data were evaluated by the similarity index, as shown in FIG. 11C. Methods in accordance with some embodiments of the present disclosure resulted in significantly higher similarity to the high SNR results.

Figure 12:
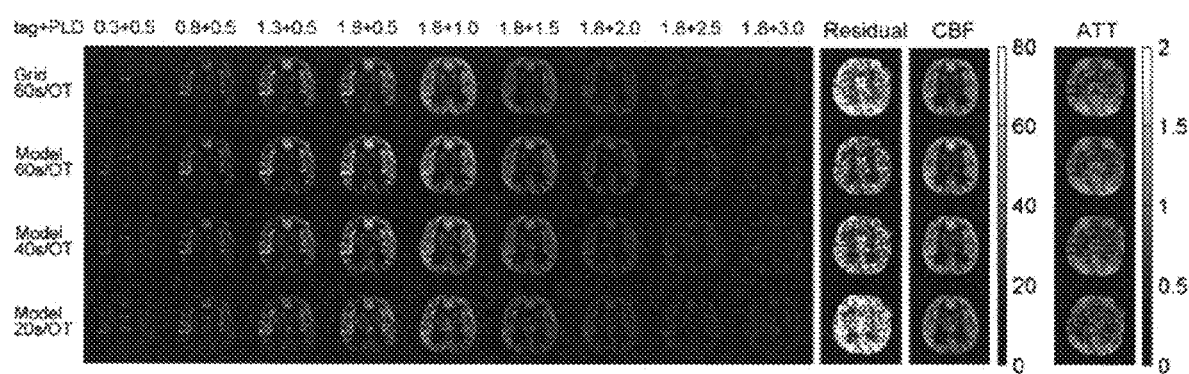
FIG. 12 illustrates accelerated dynamic ASL with model-based reconstruction, single-shot 3D spiral k-space trajectories and background suppression. With a scan time of 60 s/OT measurement, the model-based reconstruction method in accordance with some embodiments of the present disclosure reduced the background noise and model residual (mean residual=4.6 $e^{-6}$), compared with conventional gridding reconstruction (mean residual=7.1 $e^{-6}$). The method maintained the image quality with a scan time of 40 s/OT (mean residual=5.7 $e^{-6}$) and provided moderate image quality with a 20 s/OT measurement (mean residual=9.5 $e^{-6}$). Units: Dynamic model fitting residual (a.u.); CBF maps (ml/100 g/min); ATT maps (seconds).
Figure 15:
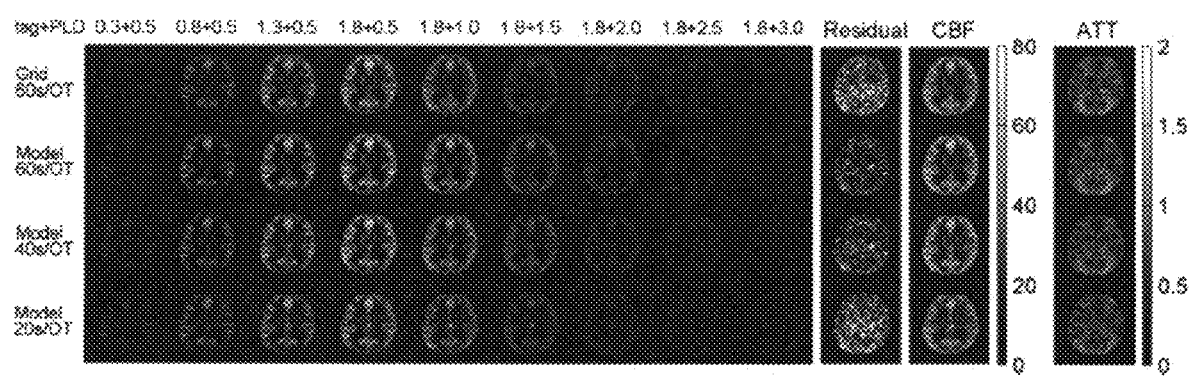
FIG. 15 illustrates a second case of accelerated dynamic ASL with model-based reconstruction, single-shot 3D spiral k-space trajectories and background suppression. Results from the first case are shown in FIG. 12. The residual in the 60 s scan and conventional reconstruction with gridding method (mean residual=4.2 $e^{-6}$) was reduced by the model-based constraint (mean residual=2.3 $e^{-6}$). The quality of images was maintained with 40 s/OT (mean residual=2.7

FIGS. 12 and 15 show the experimental results using the accelerated dynamic ASL protocol with single-shot 3D stack-of-spiral k-space trajectories and background suppression. Methods in accordance with some embodiments of the present disclosure reduced the background noise and model regression residual in the 60 s/OT scan. With an acceleration factor of 1.5, methods in accordance with some embodiments of the present disclosure largely maintained the image quality and accuracy of the CBF map when the scan time was reduced to 40 s/OT. Acceleration by a factor of 3 further reduced the scan time to 20 s per OT measurement. It resulted in more error in the CBF calculation, but even this short scan time yielded high quality for the ASL images and CBF map.

Figure 13:
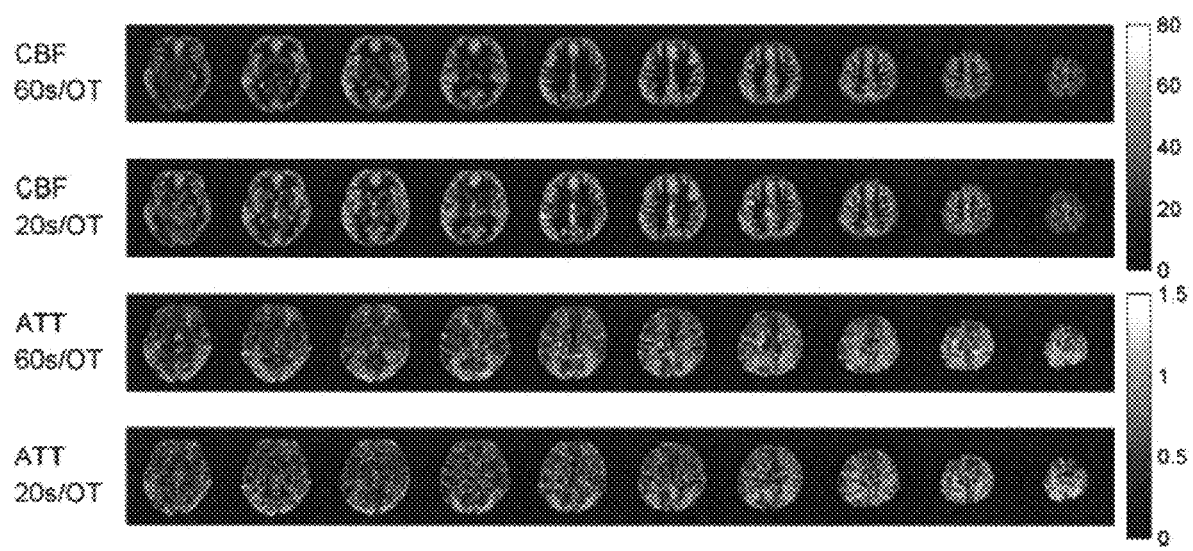
FIG. 13 illustrates CBF and ATT maps for a second case of accelerated dynamic ASL. CBF maps ((ml/100 g/min)). ATT maps (seconds).

In FIG. 13, the 3D coverage of dynamic ASL results in the second case is shown (see discussion of FIG. 15 below), with 20 s per frame scan and model-based reconstruction. The accelerated protocol had somewhat lower SNR in the white matter region as expected. Nonetheless, methods in accordance with some embodiments of the present disclosure yielded high quality dynamic 3D ASL images and parameter maps from nine perfusion phases in three minutes.

Additional Results

Standard Dynamic ASL Protocol

Image reconstruction techniques in accordance with some embodiments of the present disclosure were validated by comparison to a standard ASL imaging protocol with background suppression and conventional image reconstruction. Two volunteers were imaged with the following protocol. The 3D stack-of-spirals trajectory was implemented with three interleaved constant density spirals with 6-ms readouts. The FOV was 200 mm and the in-plane resolution was 4×4 mm$^2$. 24 slices with thickness 4 mm were acquired. TR was 5.0-5.5 s and TE was 23 ms. Control and label images were acquired with two averages, resulting in a scan time of approximately 60 s per OT measurement. Nine measurements were acquired with the OTs given in Table 2 (800, 1300, 1800, 2300, 2800, 3300, 3800, 4300, and 4800 ms).

Figure 14:
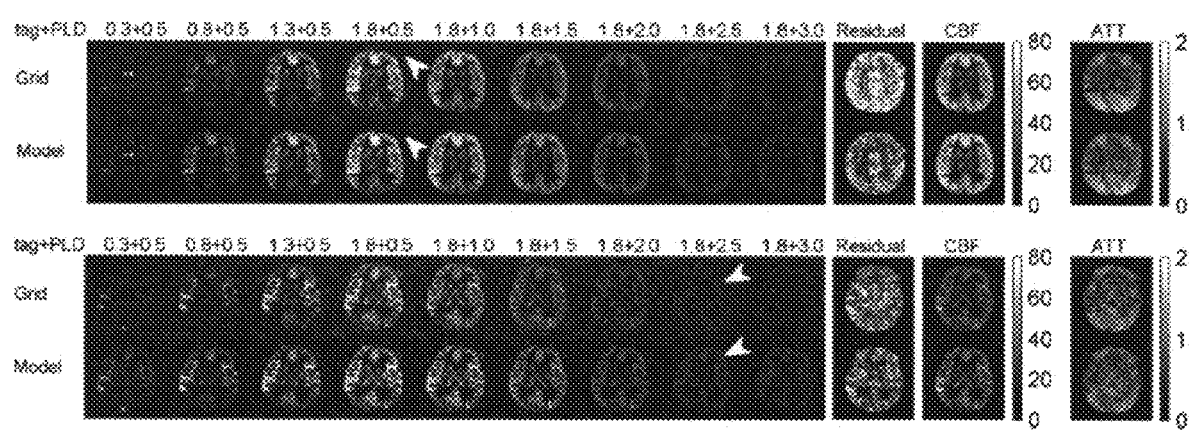
FIG. 14 shows images indicating performance of model-based image reconstruction on dynamic ASL images with background suppression for two volunteers. Each image was reconstructed using the standard gridding method and a model-based image reconstruction method in accordance with some embodiments of the present disclosure. For each subject, the top two rows show ASL images at 9 OTs, and the bottom two rows show the CBF and ATT maps calculated from these images using different methods. The arrows illustrate regions with improved SNR with the model-based image reconstruction. The model-based constraint suppressed background noise and reduced the residual in perfusion model regression. Units: dynamic model fitting residual (a.u.); CBF maps (ml/100 g/min); ATT maps (seconds).

FIG. 14 shows the performance of model-based image reconstruction on two volunteers' dynamic ASL scans with background suppression and constant-density spiral readouts. With background suppression, ASL images have good SNR at PLD=0.5, 1.0 and 1.5 seconds, with a 60 s scan per OT measurement. Compared with the standard ASL reconstruction method, methods in accordance with some embodiments of the present disclosure further suppressed the background noise in the ASL images (as highlighted by the arrows in the first volunteer's results) and provided better contrast between white matter and gray matter. It also recovered missing structures, as highlighted by the arrows in the second volunteer's results. More importantly, methods in accordance with some embodiments of the present disclosure largely reduced the residual in the model regression in both cases, corresponding to more accurate CBF and ATT maps.

Accelerated Dynamic ASL Protocol

FIG. 15 shows the results from a scan of a second volunteer using the accelerated dynamic ASL protocol. The results can be compared to those of FIG. 12. In particular, FIG. 15 shows the second case of accelerated dynamic ASL with model-based reconstruction, single-shot 3D spiral k-space trajectories and background suppression. Results from the first case are shown in FIG. 12. The residual in the 60s scan and conventional reconstruction with gridding method (mean residual=4.2 e$^{-6}$) was reduced by the model-based constraint (mean residual=2.3 e$^{-6}$). The quality of images was maintained with 40 s/OT (mean residual=2.7 e$^{-6}$) and 20 s/OT (mean residual=4.3 e$^{-6}$). Units: Dynamic model fitting residual (a.u.); CBF maps (ml/100 g/min); ATT maps (seconds).

Discussion

As described above, the present disclosure relates, in some aspects, to model-based image reconstruction for dynamic ASL perfusion imaging. Some embodiments of methods for model-based image reconstruction in accordance with the present disclosure were combined with single-shot 3D spiral acquisition and parallel imaging, yielding whole-brain dynamic ASL image acquisition in 20 seconds per time frame with an acceleration factor of 3. Prior knowledge of the dynamic ASL signal time course was exploited to distinguish the ASL signal from noise and random motion artifacts. The model-based image reconstruction methods improved ASL image quality and robustness and yielded accurate CBF estimates.

The present disclosure demonstrates, in accordance with some aspects, the acceleration of spiral k-space scanning methods using non-Cartesian parallel image reconstruction. This enables single-shot 3D spiral ASL image acquisition with sufficient spatial resolution, which in turn increases robustness to motion. The value of single-shot 3D imaging using parallel imaging has previously been demonstrated using 3D GRASE techniques (Wang et al., 2013). The present disclosure, in accordance with some aspects, demonstrates further improvements in image quality and parameter map accuracy by combining parallel imaging with model-based compressed sensing reconstruction.

As a reconstruction strategy, methods according to some embodiments of the present disclosure are compatible with most current techniques in dynamic ASL. While this study focused on spiral scanning, methods in accordance with some embodiments of the present disclosure may be adapted to use Cartesian readouts, such as 2D echo planar imaging or 3D GRASE. Background suppression was used in some of the experiments described herein to further suppress artifacts and improve image quality. While model-based reconstruction intrinsically suppresses artifacts, motion compensation may further improve the robustness. Methods in accordance with some embodiments of the present disclosure may be combined with new RF labeling pulse techniques, such as Hadamard encoding (Dai et al., 2013; J. A. Wells et al., 2010).

Model-based sparsity assumes the signal in each pixel follows a given dynamic ASL model, with the parameters of the model varying from pixel to pixel. Although CBF is a linear scale factor in the dynamic model used in studies described herein, the model is a nonlinear function of ATT. Therefore, in accordance with some embodiments of the present disclosure, a dictionary learning method was used, which provides a general approach for model-based reconstruction. This method can easily be adapted to other ASL models. The basic CASL model (Buxton et al., 1998) was used. Other models may describe perfusion by including an arterial input function (AIF) with dispersion (Calamante, 2013) or a measured AIF (Petersen et al., 2006).

The K-SVD method enforces the sparsity of the low-dimensional signal of ASL using an over-complete dictionary. The training data set included signal prototypes based on all reasonable values of the perfusion parameters (CBF and ATT). More accurate parameter ranges can be determined based upon a particular application, which can improve the sparsity and accuracy of representation in the dictionary. More prototypes in the K-SVD dictionary may further improve the sparse representation. As described herein, minor differences were noticed between dictionary sizes ranging from 32 to 512. Other parameters in the perfusion model may be assumed as prior knowledge, which are conventionally used in model fitting. The dictionary in accordance with some embodiments is resistant to the error of scaling parameters, such as $\alpha$, because the 'learning' process of the elements in dictionary is normalized. This is also true for the DC component, which is removed before dictionary training.

In some embodiments of the present disclosure described herein, direct model fitting was used to calculate CBF and ATT. The dictionary training can be also seen as a method to further simplify the model. To further improve the estimation, a simple model may be used to constrain the reconstruction, and then a more comprehensive model may be used for quantification, which may account for variations in model parameters. For example, it has been reported that a Bayesian model can improve the estimation of CBF (Chappell et al., 2009; Santos et al., 2011). These methods may be combined with various aspects of methods in accordance with the present disclosure to improve estimation of perfusion parameters.

The TV sparsity used in studies described herein is a technique commonly used in MR anatomical image reconstruction. However, the weight of the TV sparsity term was carefully chosen for ASL images. The optimal weights for the sparsity terms depend on the SNR level and the amount of motion, but the weights were not adopted on an image-by-image basis. An improperly weighted sparsity term can result in either image artifacts (by overweighting sparsity) or limited improvement (by underweighting sparsity).

In the compressed sensing reconstruction, the model-based sparsity can limit the way the initial k-space data y is prepared. Perfusion contrast in ASL is obtained by subtracting tagged images from control images. The low SNR in perfusion images can make it difficult to distinguish signal from noise. Therefore, to maximize the performance of spatial sparsity, the compressed sensing reconstruction may be applied to control and label images separately prior to subtraction. However, because the ASL signal is less than 1% of normal MR images, the dynamic evolution of ASL is too small to extract from the background signal before subtraction, so it may be difficult to exploit model-based sparsity based on component images. Therefore, in some embodiments, the k-space data of the label images was subtracted from that of the control images as the first step in the image reconstruction. This complex subtraction may be less robust than magnitude subtraction, because it is more sensitive to variations in signal phase.

In some embodiments of the present disclosure, a pCASL tagging method was used with the length of the tagging pulse reduced for early observation times. This tagging scheme was combined with a new general weighted-delay method of calculating perfusion maps. The combination of these two methods made it possible to begin measuring the ASL signal when only part of the blood bolus has arrived at the tissue of interest (Table 1). This in turn makes it possible to catch the rising edge of the perfusion signal and to detect short ATT values. Changing the length of the tagging pulse has advantages in the design of dynamic pCASL experiments. An alternative may be a design with constant perfusion bolus duration and variable post-label delay.

Acceleration factors quoted herein may be defined based on k-space undersampling factors, and thus measure the reduction in the minimum scan time relative to a fully-sampled scan that uses a conventional image reconstruction. This is one measure of the performance of methods in accordance with some embodiments of the present disclosure, but it is also important to consider the effect of such methods on the SNR of the ASL images and on the accuracy of the resulting CBF maps. Because compressed sensing is a not a linear algorithm, model-based reconstruction in accordance with some embodiments of the present disclosure canh ave more effect on the first and last frames of a dynamic image set than on the central high-SNR frames, as shown in FIGS. 12, 14, and 15. In addition, because methods in accordance with some embodiments of the present disclosure reduce motion artifacts, this can also contribute to an improvement in the apparent SNR. Experimentally, it was observed that CBF accuracy is better with an acceleration factor of 1.5 using methods in accordance with some embodiments of the present disclosure than with fully sampled data reconstructed using gridding. This is quantified by the mean CBF fitting residual in the captions of FIGS. 12 and 15. With an acceleration factor of 3, the accuracy is somewhat lower in FIG. 12 and slightly lower in FIG. 15. Thus, based on this data, an acceleration factor between 2 and 3 can be possible using this method without loss of accuracy.

Studies described herein used equally spaced observation times. However, CBF estimation accuracy may be improved by optimal observation-time design (Xie et al., 2008; Zhao and Meyer, 2012, 2013). Non-equally-spaced sampling in the parameter encoding space might break the assumptions of some sparsity constraints, such as temporal TV, but it can be adapted into model-based sparsity by proper dictionary training.

The computation time for model-based image reconstruction methods in accordance with some embodiments disclosure herein may be reduced by optimizing the algorithm, implementing it in C/C++, and employing a graphics processing unit (Murphy et al., 2012). The numerical phantom used in the simulations described herein was used to prove concepts of model-based reconstruction. Methods in accordance with some embodiments of the present disclosure enforce model-based sparsity at each pixel. Therefore, partial volume effects should have a minor impact on the conclusions drawn from the simulations. A related point is that an improved model including partial volume effects (Chappell et al., 2011) could be incorporated into methods in accordance with some embodiments of the present disclosure for the quantification of CBF.

CONCLUSION

The specific configurations, choice of materials and the size and shape of various elements can be varied according to particular design specifications or constraints requiring a system or method constructed according to the principles of the present disclosure. Such changes are intended to be embraced within the scope of the present disclosure. The presently disclosed embodiments, therefore, are considered in all respects to be illustrative and not restrictive. The patentable scope of certain embodiments of the present disclosure is indicated by the appended claims, rather than the foregoing description, and all changes that come within the meaning and range of equivalents thereof are intended to be embraced therein.

REFERENCE LIST

Aharon, M., Elad, M., Bruckstein, A., 2006. K-SVD: An Algorithm for Designing Overcomplete Dictionaries for Sparse Representation. *IEEE Trans. Signal Process.* 54, 4311-4322.

Alsop, D. C., Detre, J. a, 1996. Reduced transit-time sensitivity in noninvasive magnetic resonance imaging of human cerebral blood flow. *J. Cereb. Blood Flow Metab.* 16, 1236-1249.

Alsop, D. C., Detre, J. a., Golay, X., Günther, M., Hendrikse, J., Hernandez-Garcia, L., Lu, H., Macintosh, B. J., Parkes, L. M., Smits, M., van Osch, M. J. P., Wang, D. J. J., Wong, E. C., Zaharchuk, G., 2015. Recommended implementation of arterial spin-labeled perfusion MRI for clinical applications: A consensus of the ISMRM perfusion study group and the european consortium for ASL in dementia. *Magn. Reson. Med.* 73, 102-116.

Ashburner, J., Friston, K. J., 2005. Unified segmentation. *Neuroimage* 26, 839-851.

Asllani, I., Habeck, C., Borogovac, A., Brown, T. R., Brickman, A. M., Stern, Y., 2009. Separating function from structure in perfusion imaging of the aging brain. *Hum. Brain Mapp.* 30, 2927-35.

Bibic, A., Knutsson, L., Ståhlberg, F., Wirestam, R., 2010. Denoising of arterial spin labeling data: Wavelet-domain filtering compared with gaussian smoothing. *Magn. Reson. Mater. Physics, Biol. Med.* 23, 125-137.

Borogovac, A., Asllani, I., 2012. Arterial Spin Labeling (ASL) fMRI: advantages, theoretical constrains, and experimental challenges in neurosciences. *Int. J. Biomed. Imaging* 2012, 818456.

Buxton, R. B., Frank, L. R., Wong, E. C., Siewert, B., Warach, S., Edelman, R. R., 1998. A general kinetic model for quantitative perfusion imaging with arterial spin labeling. *Magn. Reson. Med.* 40, 383-396.

Calamante, F., 2013. Arterial input function in perfusion MRI: A comprehensive review. *Prog. Nucl. Magn. Reson. Spectrosc.* 74, 1-32.

Chappell, M. A., Groves, A. R., Macintosh, B. J., Donahue, M. J., Jezzard, P., Woolrich, M. W., 2011. Partial volume correction of multiple inversion time arterial spin labeling MRI data. *Magn. Reson. Med.* 65, 1173-1183.

Chappell, M. A., Groves, A. R., Whitcher, B., Woolrich, M. W., 2009. Variational Bayesian Inference for a Nonlinear Forward Model. *IEEE Trans. Signal Process.* 57, 223-236.

Dai, W., Garcia, D., de Bazelaire, C., Alsop, D. C., 2008. Continuous Flow-Driven Inversion for Arterial Spin Labeling Using Pulsed Radio Frequency and Gradient Fields. *Magn. Reson. Med.* 60, 1488-1497.

Dai, W., Robson, P. M., Shankaranarayanan, A., Alsop, D. C., 2012. Reduced resolution transit delay prescan for quantitative continuous arterial spin labeling perfusion imaging. *Magn. Reson. Med.* 67, 1252-1265.

Dai, W., Robson, P. M., Shankaranarayanan, A., Alsop, D. C., 2010. Modified pulsed continuous arterial spin labeling for labeling of a single artery. *Magn. Reson. Med.* 64, 975-982.

Dai, W., Shankaranarayanan, A., Alsop, D. C., 2013. Volumetric measurement of perfusion and arterial transit delay using hadamard encoded continuous arterial spin labeling. *Magn. Reson. Med.* 69, 1014-1022.

Detre, J. a, Wang, J., 2002. Technical aspects and utility of fMRI using BOLD and ASL. *Clin. Neurophysiol.* 113, 621-34.

Detre, J. A., Leigh, J. S., Williams, D. S., Koretsky, A. P., Leight, J. S., 1992. Perfusion imaging. *Magn. Reson. Med.* 23, 37-45.

Duhamel, G., de Bazelaire, C., Alsop, D. C., 2003. Evaluation of systematic quantification errors in velocity-selective arterial spin labeling of the brain. *Magn. Reson. Med.* 50, 145-153.

Fielden, S. W., Mugler, J. P., Hagspiel, K. D., Norton, P. T., Kramer, C. M., Meyer, C. H., 2014. Noncontrast peripheral MRA with spiral echo train imaging. *Magn. Reson. Med.*

Hasebroock, K. M., Serkova, N. J., 2009. Toxicity of MRI and CT contrast agents. *Expert Opin. Drug Metab. Toxicol.* 5, 403-16.

Huang, C., Graff, C. G., Clarkson, E. W., Bilgin, A., Altbach, M. I., 2012. T2 mapping from highly undersampled data by reconstruction of principal component coefficient maps using compressed sensing. *Magn. Reson. Med.* 67, 1355-1366.

Lingala, S. G., Hu, Y., Dibella, E., Jacob, M., 2011. Accelerated dynamic MRI exploiting sparsity and low-rank structure: k-t SLR. *IEEE Trans. Med. Imaging* 30, 1042-1054.

Lu, H., Clingman, C., Golay, X., Zijl, P. C. M. Van, 2004. Determining the Longitudinal Relaxation Time (T1) of Blood at 3.0 Tesla. 682, 679-682.

Lustig, M., Donoho, D., Pauly, J. M., 2007. Sparse MRI: The application of compressed sensing for rapid MR imaging. *Magn. Reson. Med.* 58, 1182-1195.

Lustig, M., Pauly, J. M., 2010. SPIRiT: Iterative self-consistent parallel imaging reconstruction from arbitrary k-space. *Magn. Reson. Med.* 64, 457-471.

Macintosh, B. J., Marquardt, L., Schulz, U. G., Jezzard, P., Rothwell, P. M., 2012. Hemodynamic alterations in vertebrobasilar large artery disease assessed by arterial spin-labeling M R imaging. *AJNR. Am. J. Neuroradiol.* 33, 1939-44.

Maleki, N., Dai, W., Alsop, D.C., 2011. Optimization of background suppression for arterial spin labeling perfusion imaging. *MAGMA* 25, 127-133.

Meyer, C. H., Zhao, L., Lustig, M., Jilwan-Nicolas, M., Wintermark, M., Mugler, J. P., Epstein, F. H., 2011.

Dual-Density and Parallel Spiral ASL for Motion Artifact Reduction. *Proc. Intl. Soc. Mag. Reson. Med.* 64, 3986.

Mugler, J. P., 2014. Optimized three-dimensional fast-spin-echo MRI. *J. Magn. Reson. Imaging*.

Murphy, M., Alley, M., Demmel, J., Keutzer, K., Vasanawala, S., Lustig, M., 2012. Fast $\varepsilon_1$-SPIRiT compressed sensing parallel imaging MRI: scalable parallel implementation and clinically feasible runtime. *IEEE Trans. Med. Imaging* 31, 1250-62.

Petersen, E. T., Lim, T., Golay, X., 2006. Model-free arterial spin labeling quantification approach for perfusion MRI. *Magn. Reson. Med.* 55, 219-32.

Qiu, M., Maguire, R. P., Arora, J., Planeta-Wilson, B., Weinzimmer, D., Wang, J., Wang, Y., Kim, H., Raj eevan, N., Huang, Y., Carson, R. E., Constable, R. T., Maguire, P., Constable, T., 2010. Arterial Transit Time Effects in Pulsed Arterial Spin Labeling CBF Mapping: Insight From a PET and MR Study in Normal Human Subjects. *Magn. Reson. Med.* 63, 374-384.

Rusinek, H., Brys, M., Glodzik, L., Switalski, R., Tsui, W.-H., Haas, F., Mcgorty, K. A., Chen, Q., de Leon, M. J., 2010. Hippocampal Blood Flow in Normal Aging Measured With Arterial Spin Labeling at 3T. *Magn. Reson. Med.*

Santos, N., Sanches, J. M., Sousa, I., Figueiredo, P., 2011. Optimal sampling and estimation in PASL perfusion imaging. *IEEE Trans. Biomed. Eng.* 58, 3165-74.

Wang, D. J., Alger, J. R., Qiao, J. X., Gunther, M., Pope, W. B., Saver, J. L., Salamon, N., Liebeskind, D. S., 2013. Multi-Delay Multi-Parametric Arterial Spin-Labeled Perfusion MRI in Acute Ischemic Stroke—Comparison with Dynamic Susceptibility Contrast Enhanced Perfusion Imaging. *NeuroImage Clin.* 3, 1-7.

Wang, D. J. J., Alger, J. R., Qiao, J. X., Hao, Q., Hou, S., Fiaz, R., Gunther, M., Pope, W. B., Saver, J. L., Salamon, N., Liebeskind, D. S., 2012. The value of arterial spin-labeled perfusion imaging in acute ischemic stroke: comparison with dynamic susceptibility contrast-enhanced MRI *Stroke* 43, 1018-1024.

Wang, Z., Bovik, A. C., Sheikh, H. R., Simoncelli, E. P., 2004. Image quality assessment: from error visibility to structural similarity. *IEEE Trans Image Process.* 13, 600-612.

Wells, J. a., Thomas, D. L., King, M. D., Connelly, A., Lythgoe, M. F., Calamante, F., 2010. Reduction of errors in ASL cerebral perfusion and arterial transit time maps using image de-noising. *Magn. Reson. Med.* 64, 715-724.

Wells, J. A., Lythgoe, M. F., Gadian, D. G., Ordidge, R. J., Thomas, D. L., 2010. In Vivo Hadamard Encoded Continuous Arterial Spin Labeling (H-CASL). *Magn. Reson. Med.* 63, 1111-1118.

Wu, W. C., Fernández-Seara, M., Detre, J. A., Wehrli, F. W., Wang, J., 2007. A theoretical and experimental investigation of the tagging efficiency of pseudocontinuous arterial spin labeling. *Magn. Reson. Med.* 58, 1020-1027.

Xie, J., Gallichan, D., Gunn, R. N., Jezzard, P., 2008. Optimal design of pulsed arterial spin labeling MRI experiments. *Magn. Reson. Med.* 59, 826-834.

Ye, F. Q., Frank, J. A., Weinberger, D. R., McLaughlin, A. C., 2000. Noise Reduction in 3D Perfusion Imaging by Attenuating the Static Signal in Arterial Spin Tagging (ASSIST). *Magn. Reson. Med.* 44, 92-100.

Yoshiura, T., Hiwatashi, A., Yamashita, K., Ohyagi, Y., Monji, A., Takayama, Y., Nagao, E., Kamano, H., Noguchi, T., Honda, H., 2009. Simultaneous Measurement of Arterial Transit Time, Arterial Blood Volume, and Cerebral Blood Flow Using Arterial Spin-Labeling in Patients with Alzheimer Disease. *Am. J. Neuroradiol.* 30, 1388-1393.

Zhao, L., Chen, X., Fielden, S. W., Epstein, F. H., III, J. P. M., Pfeuffer, J., Nicolas-jilwan, M., Wintermark, M., Meyer, C. H., 2012. Accelerated Kinetic ASL using 3D Spiral TSE and Compressed Sensing. Proc. Intl. Soc. Mag. Reson. Med. 498, 1997.

Zhao, L., Fielden, S. W., Chen, X., Iii, J. P. M., Pfeuffer, J., Nicolas-jilwan, M., Wintermark, M., Meyer, C. H., John P. Mugler, 2013. Accelerated 3DPCASL using compressed sensing. *Proc. Intl. Soc. Mag. Reson. Med.* 21, 2157.

Zhao, L., Meyer, C. H., 2013. Optimal PLD design and maximum likelihood CBF estimation for dynamic PCASL with Rician noise. *Proc. Intl. Soc. Mag. Reson. Med.* 2164.

Zhao, L., Meyer, C. H., 2012. Optimal kinetic PASL design and CBF estimation with low SNR and Rician noise. *Proc. Intl. Soc. Mag. Reson. Med.* 3494.

What is claimed is:

1. A method for dynamic arterial spin labeling (ASL) magnetic resonance imaging (MRI), comprising:
   acquiring, using a magnetic resonance imaging system, magnetic resonance data associated with an area of interest of a subject, wherein the magnetic resonance data comprises data associated with arterial spin labeling (ASL) of the area of interest; and
   performing, using one or more processors, image reconstruction on the acquired resonance data, comprising compressed sensing enforcing a model-based sparsity constraint, wherein the model-based sparsity constraint is based on an ASL signal prototype dictionary.

2. The method of claim 1, wherein the ASL signal prototype dictionary is a trained dictionary representing expected ASL signals associated with tissue pixels following an ASL signal evolution pattern.

3. The method of claim 2, wherein enforcing the model-based sparsity constraint comprises representing multiple observation time (multi-OT) ASL images by the dictionary, pixel by pixel.

4. The method of claim 2, wherein the ASL signal prototype dictionary is built iteratively from a training set, using a K-SVD technique.

5. The method of claim 1, wherein the image reconstruction further comprises enforcing at least one spatial sparsity constraint.

6. The method of claim 5, wherein the at least one spatial sparsity constraint comprises a total variation (TV) constraint.

7. The method of claim 1, wherein acquiring the magnetic resonance data comprises using a multi-dimensional turbo spin echo (TSE) pulse sequence.

8. The method of claim 1, wherein the multi-dimensional turbo spin echo (TSE) pulse sequence is a single-shot TSE pulse sequence.

9. The method of claim 1, wherein the multi-dimensional turbo spin echo (TSE) pulse sequence is a multi-shot TSE pulse sequence.

10. The method of claim 1, wherein acquiring the magnetic resonance data comprises parallel imaging.

11. The method of claim 1, wherein acquiring the magnetic resonance data comprises spiral sampling with variable density spiral k-space trajectories.

12. The method of claim 11, wherein the variable density spiral k-space trajectories comprise dual-density spiral k-space trajectories.

13. The method of claim 1, wherein the data associated with the arterial spin labeling of the area of interest comprises data obtained using multiple observation time (multi-OT) pseudocontinuous arterial spin labeling (PCASL).

14. The method of claim 13, wherein the multiple observation times are configured by varying labeling duration and post label delay of PCASL.

15. The method of claim 1, further comprising estimating arterial transit time (ATT) from multiple observation time (multi-OT) pseudocontinuous arterial spin labeling (PCASL) images by applying a weighted average calibration.

16. The method of claim 1, further comprising determining at least one characteristic of a physiological activity in the area of interest based on the acquired magnetic resonance data.

17. The method of claim 16, wherein determining the at least one characteristic of the physiological activity comprises determining cerebral blood flow (CBF).

18. The method of claim 16, wherein determining the at least one characteristic of the physiological activity comprises determining arterial transit time (ATT).

19. A system for dynamic arterial spin labeling (ASL) magnetic resonance imaging (MRI), comprising:
    a magnetic resonance imaging data acquisition device configured to acquire magnetic resonance data associated with an area of interest of a subject, wherein the magnetic resonance data comprises data associated with arterial spin labeling (ASL) of the area of interest; and
    one or more processors configured to cause the system to perform functions comprising performing image reconstruction on the acquired resonance data, the image reconstruction comprising compressed sensing enforcing a model-based sparsity constraint, and wherein the model-based sparsity constraint is based on an ASL signal prototype dictionary.

20. A non-transitory computer-readable medium having stored instructions that, when executed by one or more processors, cause a computing device to perform functions that comprise:
    acquiring magnetic resonance data associated with an area of interest of a subject, wherein the magnetic resonance data comprises data associated with arterial spin labeling (ASL) of the area of interest; and
    performing image reconstruction on the acquired resonance data, comprising compressed sensing enforcing a model-based sparsity constraint, wherein the model-based sparsity constraint is based on an ASL signal prototype dictionary.

* * * * *